(12) United States Patent
Myers et al.

(10) Patent No.: US 8,298,583 B2
(45) Date of Patent: Oct. 30, 2012

(54) FILM DELIVERY SYSTEM FOR TETRAHYDROLIPSTATIN

(75) Inventors: Garry L. Myers, Kingsport, TN (US); Samuel D. Hilbert, Jonesboro, TN (US); Bill J. Boone, Johnson City, TN (US)

(73) Assignee: Monosol Rx, LLC, Portage, IN (US)

( * ) Notice: Subject to any disclaimer, the term of this patent is extended or adjusted under 35 U.S.C. 154(b) by 0 days.

(21) Appl. No.: 11/975,584

(22) Filed: Oct. 19, 2007

(65) Prior Publication Data

US 2009/0104270 A1    Apr. 23, 2009

(51) Int. Cl.
*A61K 9/14* (2006.01)
*A61K 9/70* (2006.01)
*A61K 38/00* (2006.01)
*A61K 31/335* (2006.01)

(52) U.S. Cl. .......... 424/489; 424/443; 514/1.1; 514/449

(58) Field of Classification Search .................... None
See application file for complete search history.

(56) References Cited

U.S. PATENT DOCUMENTS

| | | | |
|---|---|---|---|
| 3,007,848 A | 11/1961 | Stroop | |
| 4,598,089 A | 7/1986 | Hadvary et al. | |
| 5,605,696 A | 2/1997 | Eury et al. | |
| 5,800,832 A | 9/1998 | Tapolsky et al. | |
| 5,806,284 A | 9/1998 | Gifford | |
| 6,004,996 A | 12/1999 | Shah et al. | |
| 6,072,100 A | 6/2000 | Mooney et al. | |
| 6,375,963 B1 | 4/2002 | Repka et al. | |
| 6,730,319 B2 * | 5/2004 | Maeder et al. | 424/464 |
| 6,800,329 B2 | 10/2004 | Horstmann et al. | |
| 6,824,829 B2 | 11/2004 | Berry et al. | |
| 7,005,142 B2 | 2/2006 | Leon et al. | |
| 7,579,019 B2 | 8/2009 | Tapolsky et al. | |
| 2003/0107149 A1 * | 6/2003 | Yang et al. | 264/134 |
| 2003/0147956 A1 | 8/2003 | Shefer et al. | |
| 2004/0096569 A1 | 5/2004 | Barkalow et al. | |
| 2004/0191302 A1 | 9/2004 | Davidson | |
| 2005/0048102 A1 | 3/2005 | Tapolsky et al. | |
| 2006/0210610 A1 | 9/2006 | Davidson et al. | |
| 2006/0246141 A1 * | 11/2006 | Liversidge et al. | 424/489 |
| 2007/0087036 A1 | 4/2007 | Durshlag et al. | |
| 2007/0148097 A1 | 6/2007 | Finn et al. | |

FOREIGN PATENT DOCUMENTS

| | | |
|---|---|---|
| EP | 0598606 B1 | 6/1999 |
| JP | 62126950 | 6/1987 |
| JP | 02265444 | 10/1990 |
| JP | 05147140 | 6/1993 |
| JP | 07322812 | 12/1995 |
| JP | 2001279100 | 10/2001 |
| WO | 03/030883 A1 | 4/2003 |
| WO | 2004/087084 A1 | 10/2004 |
| WO | 2006/031209 A1 | 3/2006 |
| WO | 2008011194 A2 | 1/2008 |

OTHER PUBLICATIONS

Search Report for PCT/US08/80404 dated Dec. 22, 2009.
Hadvary et al.; "Inhibition of pancreatic lipase in vitro by the covalent inhibitor tetrahydrolipstatin", Biochem J. (1988), vol. 256, pp. 357-361.
Ko et al.; "Behavior of tetrahydrolipstatin in biological model membranes and emulsions", Journal of Lipid Research, (1997) vol. 38, pp. 1544-1552.
Lazaridou et al., "Thermophysical proprties of chitosan, chitosan-starch and chitosan-pullulan films near the glass transition," Carbohydrate Polymers 48: 179-190 (2002).
Repka et al., "Bioadhesive Properties of hydroxypropylcellulose topical films produced by hot melt extrusion," Journal of Controlled Release, 70: 341-351 (2001).
Repka et al., "Influence of Vitamin E TPGS on the properties of hydrophilic films produced by hot melt extrusion", International Journal of Pharmaceutics 202: 63-70 (2000).
Bowen P., Particle Size Distribution Measurement from Millimeters to Nanometers and from Rods to Platelets., Journal of Dispersion Science and Technology., vol. 23, No. 5 pp. 631-662, 2002.
Supplementary European Search Report for Application No. EP 08840684.8 dated Jul. 7, 2011.

* cited by examiner

*Primary Examiner* — Robert A Wax
*Assistant Examiner* — Jeffrey T Palenik
(74) *Attorney, Agent, or Firm* — Hoffmann & Baron, LLP

(57) ABSTRACT

The present invention includes a pharmaceutical-based film system which includes various small-scale forms of pharmaceutically active agents, including tetrahydrolipstatin, in a film base. Such forms include nanoparticles, microparticles, and combinations thereof. Methods of producing such film and providing a dosage of the pharmaceutical in a film are also provided.

46 Claims, 5 Drawing Sheets
(3 of 5 Drawing Sheet(s) Filed in Color)

FILM DELIVERY SYSTEM FOR TETRAHYDROLIPSTATIN

FIELD OF THE INVENTION

The invention relates to rapidly dissolving films and methods of their preparation. More particularly, the invention relates to rapidly dissolving films and methods of their preparation including stabilization of the pharmaceutical compound tetrahydrolipstatin in a small-scale form, which allows for quicker and more efficient dissolution and ingestion into the body, such as in the form of nanoparticles and/or microparticles.

BACKGROUND OF THE RELATED TECHNOLOGY

Active ingredients, such as drugs or pharmaceuticals, may be prepared in a tablet form to allow for accurate and consistent dosing. However, this form of preparing and dispensing medications has many disadvantages including that a large proportion of adjuvants must be added to obtain a size able to be handled, that a larger medication form requires additional storage space, and that dispensing includes counting the tablets which has a tendency for inaccuracy. In addition, many persons, estimated to be as much as 28% of the population, have difficulty swallowing tablets. While tablets may be broken into smaller pieces or even crushed as a means of overcoming swallowing difficulties, this is not a suitable solution for many tablet or pill forms. For example, crushing or destroying the tablet or pill form to facilitate ingestion, alone or in admixture with food, may also destroy controlled release properties of the tablet or pill.

As an alternative to tablets and pills, films may be used to carry active ingredients such as drugs, pharmaceuticals, and the like. However, historically films and the process of making drug delivery systems therefrom have suffered from a number of unfavorable characteristics that have not allowed them to be used in practice. Further, films have limited space within which to include a sufficient dosage amount, given the high amount of polymer required to support the film. Films are additionally more difficult to keep stable, given that most of the product is exposed. Products such as tablets and pills are denser and may be coated, generally giving more stability. As such, films for many pharmaceuticals have generally been avoided.

Films that incorporate a pharmaceutically active ingredient are disclosed in expired U.S. Pat. No. 4,136,145 to Fuchs, et al. ("Fuchs"). These films may be formed into a sheet, dried and then cut into individual doses. The Fuchs disclosure alleges the fabrication of a uniform film, which includes the combination of water-soluble polymers, surfactants, flavors, sweeteners, plasticizers and drugs. These allegedly flexible films are disclosed as being useful for oral, topical or enteral use. Examples of specific uses disclosed by Fuchs include application of the films to mucosal membrane areas of the body, including the mouth, rectal, vaginal, nasal and ear areas.

The pharmaceutical compound tetrahydrolipstatin, also known as orlistat (trade name Xenical), (2S,3S,5S)-5-[(S)-2-formamido-4-methyl-valeranyloxy]-2-hexyl-3-hexadecanoic acid lactone, is indicated for treatment of obesity in humans. Tetrahydrolipstatin is a lipase inhibitor, blocking the absorption of approximately 30% of dietary fat. It is generally used for weight loss and weight management, and can also help prevent the onset of such diseases as type 2 diabetes, hypertension, and dyslipiemia.

Tetrahydrolipstatin is generally known in the art. For example, U.S. Pat. No. 4,598,089 teaches formation of the compound and its use as an effective obesity treatment pharmaceutical. U.S. Pat. No. 4,983,746 relates to a process for the artificial synthesis of orlistat which involves producing oxetanone derivatives; and esterification of the acid derivatives with an alcohol. Tetrahydrolipstatin is naturally stabilized in a crystalline structure.

Tetrahydrolipstatin is a very lipophilic compound, and is not readily dispersed into water. It is known to be very water-insoluble in its natural crystalline state. Its melting point is approximately 44-46° C. Those skilled in the art have attempted to develop new ways to manufacture tetrahydrolipstatin in its natural form. For example, U.S. Pat. No. 6,734,314 relates to a method of manufacturing tetrahydrolipstatin in a natural form.

Although small scale drug forms may have certain advantages, very few drugs are stable by nature in such a small scale form, such as in the form of nanoparticles or microparticles. Generally, when a drug has been formed in small-scale form, it is encapsulated within a softgel or hardgel capsule or tablet. However, the use of such drugs in the small-scale form has been generally limited to the use in a capsule-based or tablet-based system. For example, U.S. Pat. No. 6,004,996 discloses an attempt to stabilize tetrahydrolipstatin in a pellet. Until now, nanoparticles were made via processes such as milling or burning, which may drastically alter the chemical nature and effect of the active agent. Thus, stabilizing a drug in the small-scale form without disrupting the active effect of the agent is desired.

Therefore, there is a need for methods and compositions for preparing and stabilizing pharmaceutical compounds in a small-scale form without the need to encapsulate the compound in a tablet or capsule. Particularly, there is a need for methods and compositions for preparing and stabilizing pharmaceutical compounds in the form of nanoparticles or microparticles. There is further a need to prepare a drug dosage form which increases the apparent solubility of the drug. The stabilized, small-scale drugs can then be incorporated into other dosage forms, such as films. The present invention fulfills these and other needs, by preparing and stabilizing pharmaceutical compounds in the form of nanoparticles and/or microparticles.

SUMMARY OF THE INVENTION

In one embodiment, the present invention provides a method of stabilizing a form of a pharmaceutical compound in small-scale form, including the steps of providing a mixture of a pharmaceutically active agent with a melting point below 100° C. and at least one water soluble polymer; dissolving at least a portion of the mixture in heated water; and evaporating the water to form a stable small-scale form of the pharmaceutically active agent.

In another embodiment, there is provided a pharmaceutical-based film composition, including pharmaceutically active tetrahydrolipstatin in a stable, small-scale form and at least one water soluble polymer.

In another embodiment, there is provided a method of stabilizing a pharmaceutically active agent in a small-scale form, including the steps of providing a mixture of a pharmaceutically active agent with a melting point below 100° C. and at least one water soluble polymer; dissolving at least a portion of the mixture in heated water; evaporating the water; and gathering the resulting residue.

In yet another embodiment, there present invention provides a method of administering a dosage form to an individual, including the steps of providing a pharmaceutical-based film, and orally administering the pharmaceutical-based film to an individual, the pharmaceutical based film including a pharmaceutically active agent in a stabilized, small-scale form and at least one water-soluble polymer.

In another embodiment, there is provided a method of preparing a pharmaceutical-based film, including the steps of providing a mixture including a pharmaceutically active agent with a melting point below 100° C. and at least one water soluble polymer; dissolving at least a portion of the mixture in heated water; removing the water to form a stable, small-scale form of the pharmaceutically active agent; and forming a film including the stable, small-scale form of the pharmaceutically active agent.

Another embodiment of the invention provides a method of administering a pharmaceutical dosage to an individual in a lesser amount than is normally required to achieve a bioequivalent result, including the steps of providing a pharmaceutical-based film including a pharmaceutical compound in stable, small-scale form, and orally administering the pharmaceutical compound to an individual.

In another embodiment, there is provided a method of treating or preventing obesity in humans, including the steps of providing a film including at least one water soluble polymer and a small-scale form of tetrahydrolipstatin, orally administering the film system to a human, where the small-scale form of tetrahydrolipstatin is absorbed into the bodily system of the human.

Another embodiment of the invention provides a method of treating or preventing obesity in humans, including the steps of providing a film system including at least one water-soluble polymer and tetrahydrolipstatin in the form of a collection of microparticles, orally administering the film system to a human, where the tetrahydrolipstatin microparticles are absorbed into the bodily system of the human.

In another embodiment, there is provided a method of treating or preventing obesity in humans, including the steps of providing a film system including at least one water-soluble polymer and tetrahydrolipstatin in the form of a collection of nanoparticles, orally administering the film system to a human, where the tetrahydrolipstatin nanoparticles are absorbed into the bodily system of the human.

The present invention, in another embodiment, provides a method of preparing a pharmaceutical-based film system, including the steps of providing a mixture including a pharmaceutically active agent with a melting point below 100° C. and at least one water soluble polymer; dissolving at least a portion of the mixture in heated water; evaporating the water to form stabilized nanoparticles of the pharmaceutically active agent; and forming a film including the nanoparticles of the pharmaceutically active agent.

In yet another embodiment, there is provided a method of preparing a pharmaceutical-based film, including the steps of providing a mixture including a pharmaceutically active agent with a melting point below 100° C. and at least one water soluble polymer; dissolving at least a portion of the mixture in heated water; evaporating the water to form stabilized microparticles of the pharmaceutically active agent; and forming a film including the microparticles of the pharmaceutically active agent.

In another embodiment, there is provided a pharmaceutical based film system including stabilized nanoparticles of tetrahydrolipstatin and at least one water-soluble polymer.

In another embodiment, there is provided a pharmaceutical based film system including stabilized microparticles of tetrahydrolipstatin and at least one water-soluble polymer.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
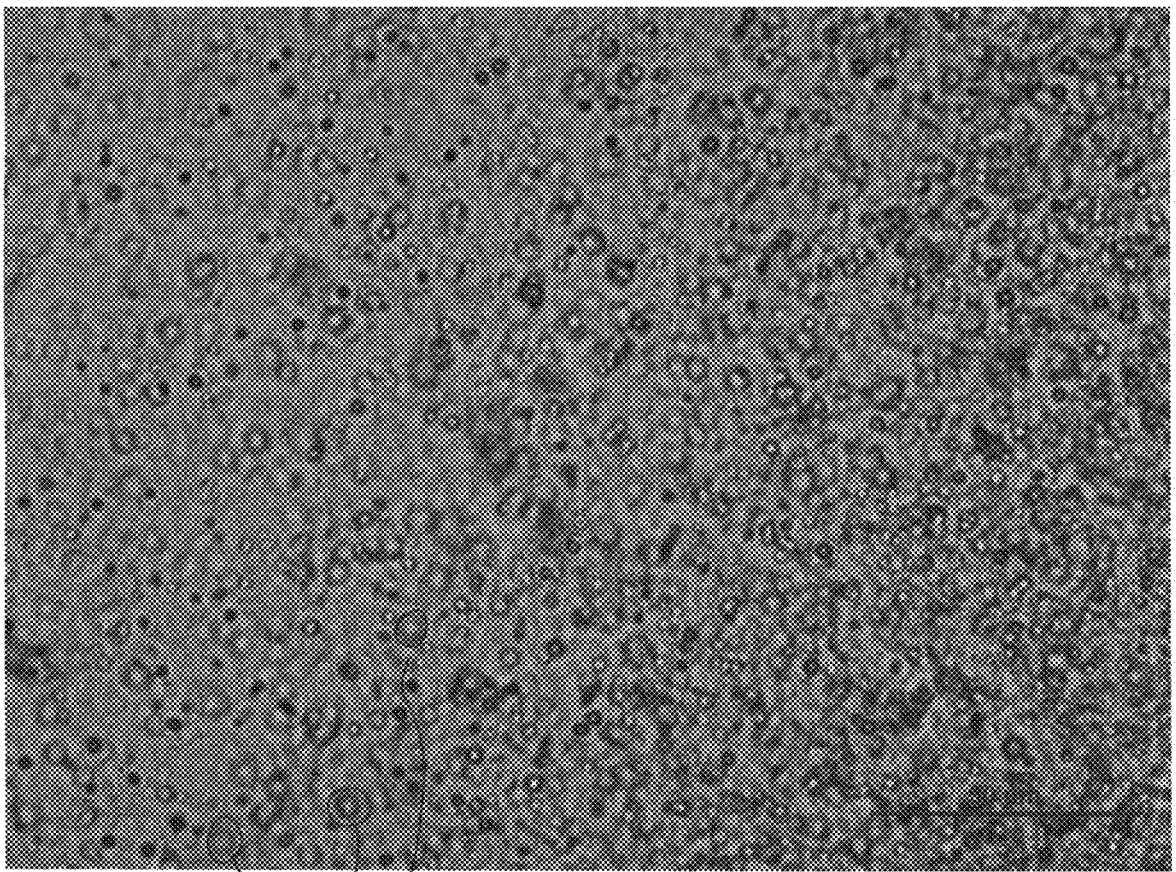
FIG. 1 shows a photomicrograph of stabilized nanoparticles of tetrahydrolipstatin prepared by the method of the present invention taken by atomic force microscopy.

The present invention relates to methods of stabilizing a small-scale form of a pharmaceutical compound. The pharmaceutical compound may include, for example, the compound in the form of nanoparticles and/or microparticles, or combinations thereof. The stabilized, small-scale compound may then be formed into a dosage form, such as a film. As used herein, "stabilized" means that the pharmaceutical compound remains in the form described until an outside force is acted upon it. The stabilized, nanoparticles and microparticles of pharmaceutical compound of the present invention do not convert into a larger form unless an outside force acts upon them, which forces the particles away from the small size and into a larger, more natural state.

As used herein, the "particle size" refers to the average diameter of the particle as measured along its widest point. As used herein, a "nanoparticle" refers to a form of the active agent wherein the diameter is less than about 100 nanometers in size. A "microparticle" refers to a form of the active agent wherein the diameter is less than about 100 microns in size. Nanoparticles and microparticles may be any shape, including spherical or otherwise. Also as used herein, the term "stability" refers to the ability of the particles to remain substantially physically stable over a period of time. Optimally, the particles should remain substantially stable in storage for about 6 months at 40° C. and 75% humidity.

The nanoparticles and microparticles of the present invention may include the active agent as well as other materials, including the water-soluble polymer and other additives which are included in the film system. Further, nanoparticles may be agglomerated together to form larger structures, including microparticles. In some embodiments, a microparticle is an agglomeration of nanoparticles. Nanoparticles and microparticles are generally referred to herein as a "small-scale form" of the active agent. It is understood that the "small scale" form of the active includes not only the active in the form of nanoparticles and microparticles, but also includes other small sizes and combinations thereof, such as agglomerated nanoparticles. As will be described in more detail below, a film system including the stabilized, small-scale active agent can be prepared with the resulting formation.

Forming the Small-Scale Form Pharmaceutically-Active Agent

As will be described in more detail below, the present invention includes the formation and stabilization of a pharmaceutically active agent in a small-scale form. The agent may be stabilized in any number of forms, including in the form of stabilized nanoparticles or microparticles, or combinations thereof. The nanoparticles and microparticles may be in the shape of spheres (i.e., nanospheres and microspheres), may be in any other shape. The nanoparticles and microparticles may be independent or they may be agglomerated together to form larger forms.

In one advantageous embodiment of the invention, there is provided a method, which includes providing a pharmaceutically active agent with a melting point below the boiling point of the solvent used. The agent may be combined with at least one polymer, desirably a water-soluble polymer, to form a mixture. The use of a polymer is desirable as it also is used to form a film after formation and stabilization of the pharmaceutically active agent. The mixture may be added to solution, and heated at or above the melting point of the pharmaceutically active agent, but below the boiling point of the solvent, to dissolve at least a portion of the agent. After removing, e.g., by evaporating or other means, the solvent from the solution, the resulting residue forms a stable and small-scale form of the pharmaceutically active agent. Preferably, the solvent used is water, but any suitable solvent may be used. The resulting residue may be in any form, including in the form of a composition of nanoparticles or microparticles, or combinations thereof, of the active agent dispersed in the polymer.

Figure 2:
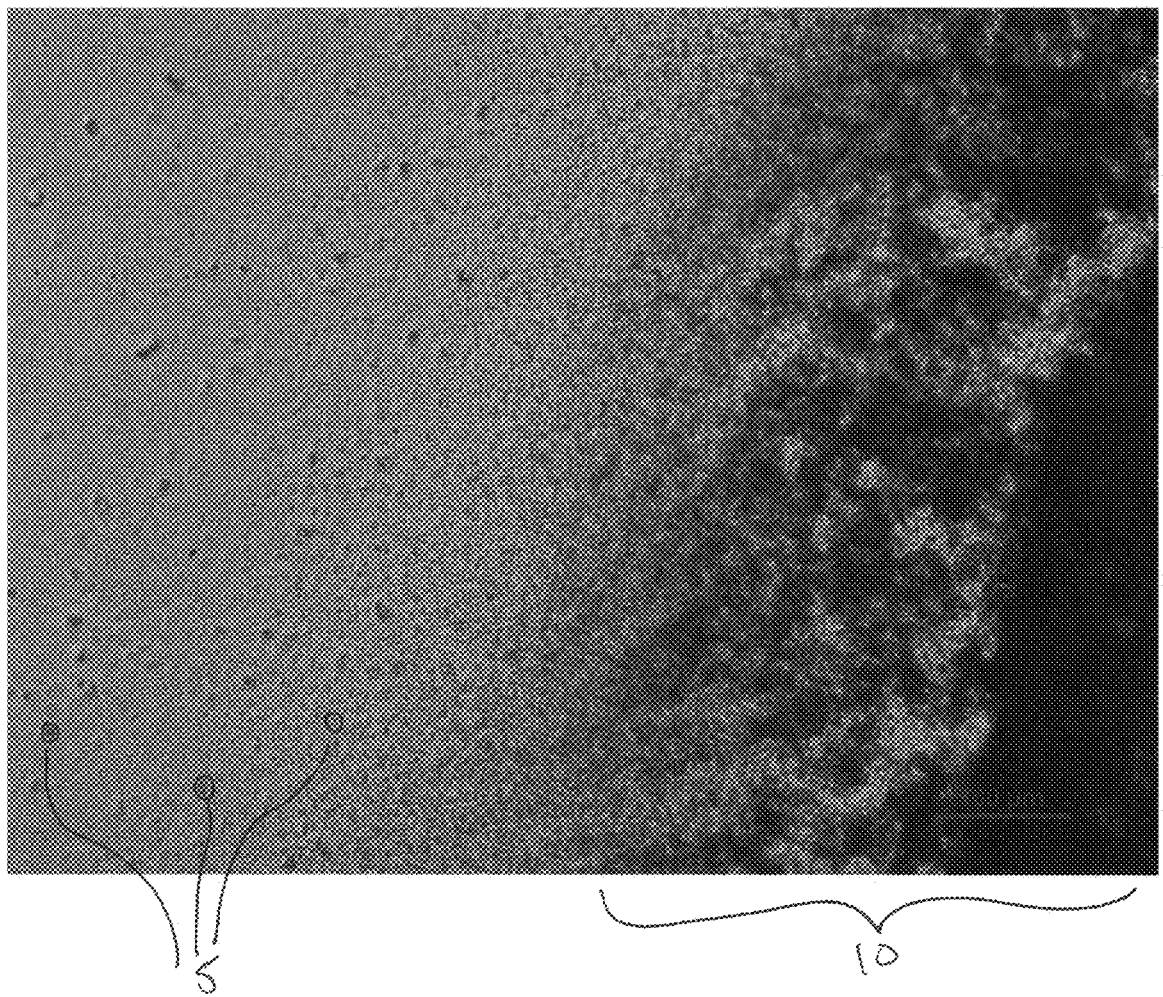
FIG. 2 shows a more close-up photomicrograph of stabilized nanoparticles of tetrahydrolipstatin prepared by the method of the present invention taken by atomic force microscopy.

Referring now to the figures, FIG. 1 is a photomicrograph depicting stabilized, nanoparticles of tetrahydrolipstatin using cross polarized light. The photomicrograph has been taken using atomic force microscopy techniques. As can be seen, FIG. 1 depicts particles 5 of active agent, appearing as transparent spheres. The particles 5 do not appear bright white, which indicates a small-scale size. Similarly, FIG. 2 is a more close-up photomicrograph of the present invention depicting stabilized nanoparticles of tetrahydrolipstatin. The photomicrograph has been taken using atomic force microscopy techniques. FIG. 2 shows a low density area indicative of a small-scale region, where the nanoparticles 5 of active agent can be seen. The region to the right of FIG. 2 shows an area of diffusion 10.

Figure 3:
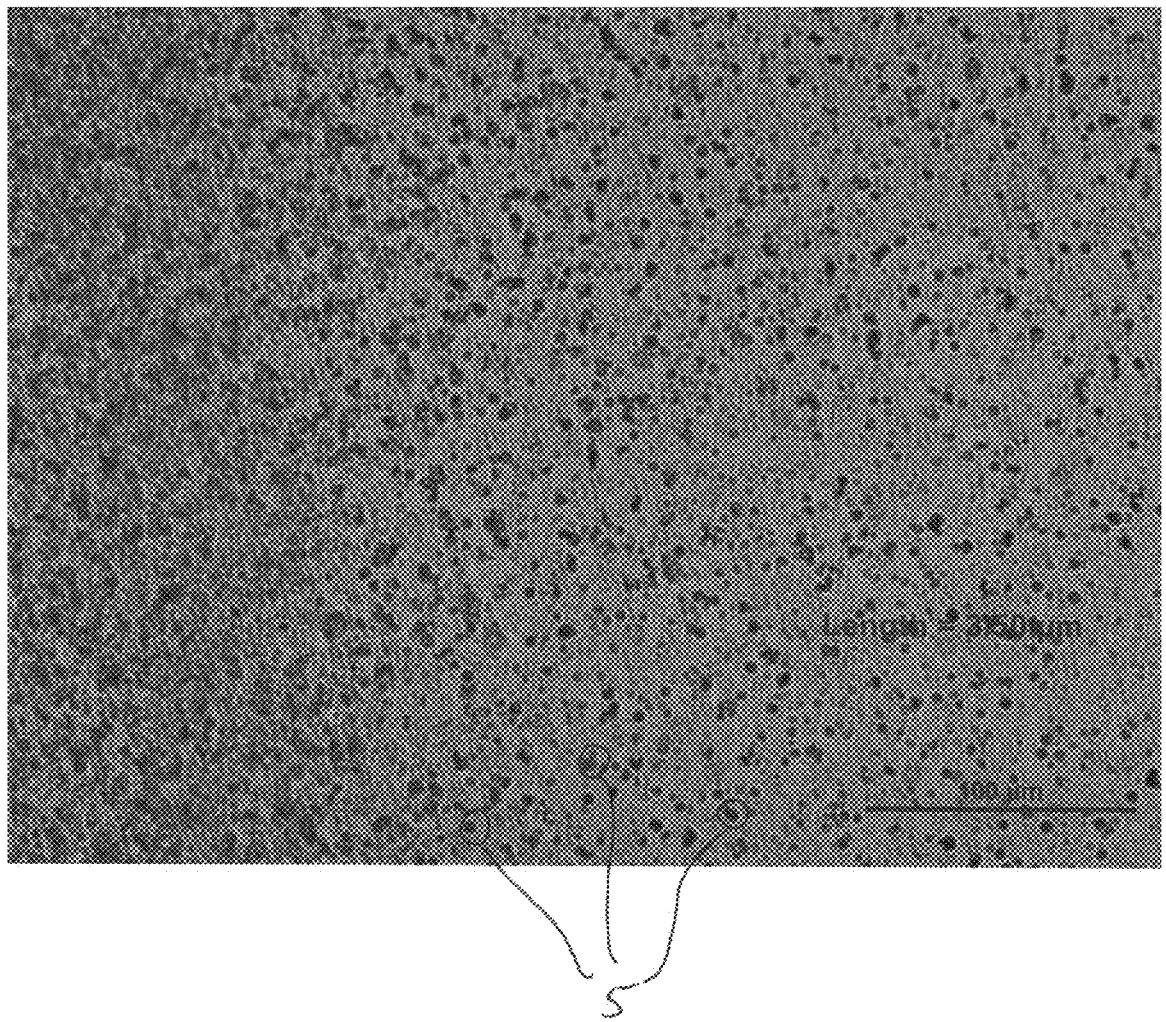
FIG. 3 shows a photomicrograph of stabilized nanoparticles of tetrahydrolipstatin prepared by the method of the present invention taken by atomic force microscopy, after water has been evaporated.

FIG. 3 is a photomicrograph depicting stabilized nanoparticles of tetrahydrolipstatin after the solvent has been evaporated. The photomicrograph has been taken using atomic force microscopy techniques. FIG. 3 clearly shows individual particles 5 that have not coalesced. This indicates that the particles 5 remain free and do not recrystallize into a larger form of the active agent. FIG. 3 shows that the active agent has been stabilized in the form of nanoparticles.

Figure 4:
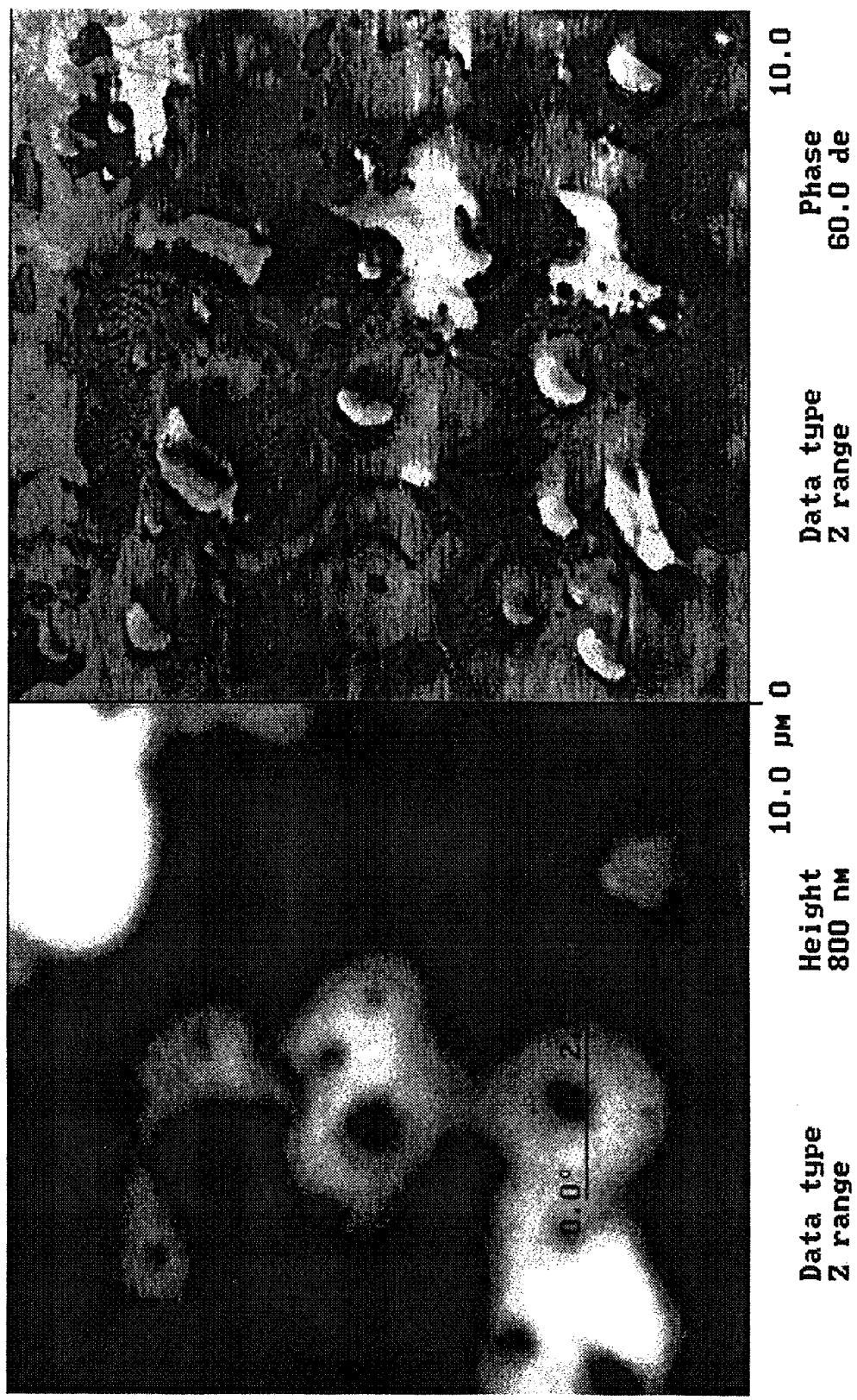
FIG. 4 shows a photomicrograph of stabilized nanoparticles of tetrahydrolipstatin manufactured pursuant to the present invention using atomic force microscopy.

FIG. 4 (labeled "tthl.str.2") shows a photomicrograph using atomic force microscopy of stabilized nanoparticles of tetrahydrolipstatin prepared pursuant to the present invention. As can be seen, one aspect of the present invention forms microspheres of active agent, which are depicted as white ball-like formations 15. The area on the left side of FIG. 4 shows a microparticle 15 of tetrahydrolipstatin with an approximate size of 2.63 µm. Desirably, the microparticles prepared as described herein have a size of from about 1 to about 6 µm, and most preferably from about 2 to about 4 µm.

Figure 5:
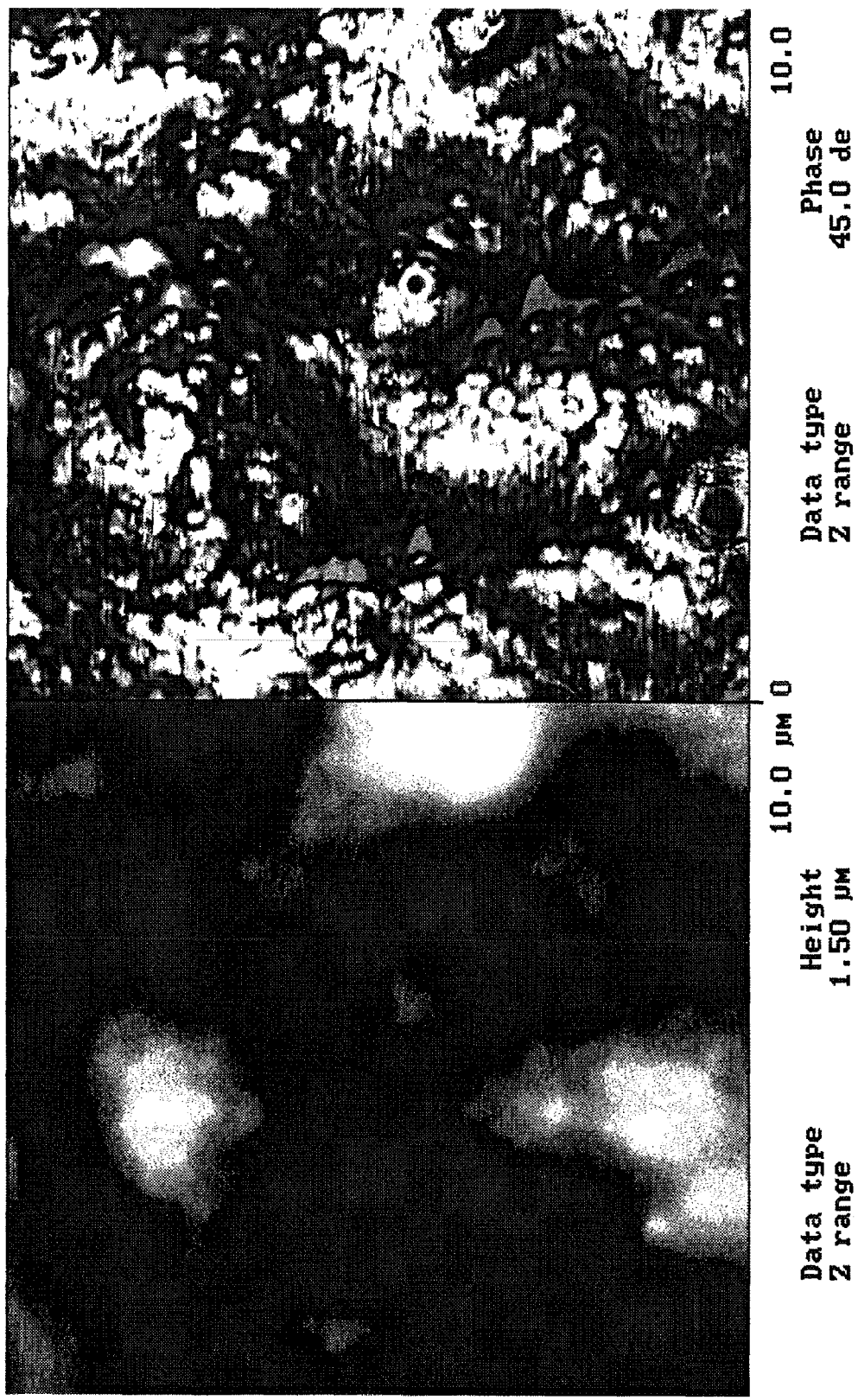
FIG. 5 shows a photomicrograph of stabilized nanoparticles of tetrahydrolipstatin manufactured pursuant to the present invention using atomic force microscopy.

FIG. 5 (labeled "tthl.dro.4") shows a photomicrograph using atomic force microscopy of stabilized nanoparticles of tetrahydrolipstatin prepared pursuant to the present invention. As can be seen in FIG. 5, the active agent is in the form of nanoparticles, which are depicted as white ball-like formations 20. Reference to FIG. 5 shows that the nanoparticles 20 are stable in formation, and do not revert to a larger size.

Formation of the film compositions of the present invention, described in more detail below, may be performed by combining all components together to form a mix, or by combining only portions of components together to form a premix, which can then be used to incorporate further components. One advantage of a pre-mix is that most, if not all of the ingredients except for the active may be combined in advance, with the active added just prior to formation of the film. This is especially important for actives that may volatize, degrade or otherwise become less effective with prolonged exposure to water, air or other polar solvents.

The pre-mix may be used in what may be referred to as a mother-daughter mix, to allow the addition of an active and subsequent formation of a film. Examples of such mixers include those described in Applicant's co-pending U.S. Publication No. 2003-0107149 A1, which is incorporated by reference in full herein. The pre-mix or master batch, which includes the polymer, polar solvent, and any other additives, except the pharmaceutical active, is added to a master batch feed tank. Then a pre-determined amount of the master batch is controllably fed to either or both of the first and second mixers. The required amount of the drug is added to the desired mixer through an opening in each of the mixers. After the drug has been blended with the master batch pre-mix for a sufficient time to provide a uniform matrix, a specific amount of the uniform matrix is then fed to a pan through the second metering pumps. A metering roller may determine the thickness of the film, and apply it to the application roller. The film is finally formed on the substrate and carried away via the support roller. The wet film is then dried using controlled bottom drying to achieve uniformity of content in the final dried film, which is described more fully below.

Pharmaceutically Active Agents

The system of the present invention includes at least one pharmaceutically-active agent. Specifically contemplated are water-insoluble pharmaceutically active compounds, especially those that are described as "sparingly soluble" and those described as "insoluble." According to *Remington's Pharmaceutical Sciences*, 18$^{th}$ Edition, page 208, Published by Philadelphia College of Pharmacy and Science, drugs that are "sparingly soluble" have a ratio of 30-100 parts of solvent for 1 part of solute, and those defined as "insoluble" have a ratio of more than 10,000 parts of solvent for 1 part of solute. Thus, the pharmaceutically active compounds of the present invention preferably have a ratio of about 30-100 parts of solvent per 1 part of solute to more than about 10,000 parts of solvent for 1 part of solute.

Desirably, the pharmaceutical agent(s) used in the present invention have a melting point of below 100° C. A particularly desirable type of useful pharmaceutical agent includes lipase inhibitors. One such lipase inhibitor is tetrahydrolipstatin. Other potential pharmaceutically active agents include lipstatin, panclicins, 2-oxy-4H-3,1-benzoxazin-4-ones, and other oxetanones. In general, any active agent may be used, so long as it has a melting point below the boiling point of the solvent used. Some non-limiting examples of potential active agents for use with the present invention include, but are not limited to, ibuprofen, nigerine, fenofibrate, ceftizoxime, chlorambucide, cyclophosphamide, econazole, ethofibrate, fennofibrate, fosfomycin, penicillin O, piribedil, pirprofen, keotprofen, lidocaine, nicorandil, and oxprenolol. Other suitable active agents would be apparent to one of ordinary skill in the art. A more pronounced effect of the invention can be seen with drugs that are more insoluble in their natural state, demonstrating the effect of nanoparticles of active compared to the natural state. Tetrahydrolipstatin as prepared by the present invention preferably has an agglomerated particle size of approximately 1 to 8 microns average diameter, and most preferably approximately 1 to 4 microns in diameter.

Composition of the Film

The stabilized nanoparticles and microparticles of the pharmaceutical compound may optionally be formed into a film dosage form. The film products in general are formed by combining a properly selected polymer and polar solvent, as well as any active ingredient or filler as desired. Desirably, the solvent content of the combination is at least about 30% by weight of the total combination. The matrix formed by this combination is formed into a film, desirably by roll coating, and then dried, desirably by a rapid and controlled drying process to maintain the compositional uniformity per unit volume of the film. More specifically, the film will maintain a non-self-aggregating uniform heterogeneity so as to avoid disrupting the uniformity of the film. The resulting film will desirably contain less than about 10% by weight solvent, more desirably less than about 8% by weight solvent, even more desirably less than about 6% by weight solvent and most desirably less than about 2%. The solvent may be water, or alternatively may be a polar organic solvent including, but not limited to, ethanol, isopropanol, acetone, methylene chloride, or combinations thereof.

Material selection for the different components of the film of the present invention may be impacted by considerations of various parameters, including rheology properties, viscosity, mixing method, casting method and drying method. Furthermore, such consideration with proper material selection provides the compositions of the present invention, including a pharmaceutical and/or cosmetic dosage form or film product having no more than a 10% variance of a pharmaceutical and/or cosmetic active per unit area. The uniformity of the invention refers to the amount of the components per unit volume remaining substantially the same. Preferably, the present invention has no more than a 10% variance in the amount of components per unit volume of the film. Desirably, the variance is less than 5%, and more desirably, less than 0.5%.

Film-Forming Polymers

Preferably, the polymer of the present invention is water soluble, but may be water soluble, water swellable, water insoluble, or a combination of one or more either water soluble, water swellable or water insoluble polymers. The polymer may include cellulose or a cellulose derivative. Specific examples of useful water soluble polymers include, but are not limited to, hydroxypropyl methylcellulose, gum acacia, gum arabic, carboxymethyl cellulose, propylene glycol, hydroxypropyl cellulose, methyl cellulose, ethyl methyl cellulose, sodium carboxy methyl cellulose, sodium alginate, propylene glycol alginate, carboxyvinyl copolymers, starch, gelatin, dextran, and combinations thereof. Specific examples of useful water insoluble polymers include, but are not limited to, hydroxypropyl ethyl cellulose, cellulose acetate phthalate, hydroxypropyl methyl cellulose phthalate and combinations thereof.

As used herein the phrase "water soluble polymer" and variants thereof refer to a polymer that is at least partially soluble in water, and desirably fully or predominantly soluble in water, or absorbs water. Polymers that absorb water are often referred to as being water swellable polymers. The materials useful with the present invention may be water soluble or water swellable at room temperature and other temperatures, such as temperatures exceeding room temperature. Moreover, the materials may be water soluble or water swellable at pressures less than atmospheric pressure. Desirably, the water soluble polymers are water soluble or water swellable having at least 20 percent by weight water uptake. Water swellable polymers having a 25 or greater percent by weight water uptake are also useful. Films or dosage forms of the present invention formed from such water soluble polymers are desirably sufficiently water soluble to be dissolvable upon contact with bodily fluids.

Other polymers useful for incorporation into the films of the present invention include biodegradable polymers, copolymers, block polymers and combinations thereof. Among the known useful polymers or polymer classes which meet the above criteria are: poly(glycolic acid) (PGA), poly (lactic acid) (PLA), polydioxanoes, polyoxalates, poly($\alpha$-esters), polyanhydrides, polyacetates, polycaprolactones, polyethylene oxide, poly(orthoesters), polyamino acids, polyaminocarbonates, polyurethanes, polycarbonates, polyamides, poly(alkyl cyanoacrylates), and mixtures and copolymers thereof. Additional useful polymers include, stereopolymers of L- and D-lactic acid, copolymers of bis(p-carboxyphenoxy) propane acid and sebacic acid, sebacic acid copolymers, copolymers of caprolactone, poly(lactic acid)/poly(glycolic acid)/polyethyleneglycol copolymers, copolymers of polyurethane and (poly(lactic acid), copolymers of polyurethane and poly(lactic acid), copolymers of $\alpha$-amino acids, copolymers of $\alpha$-amino acids and caproic acid, copolymers of $\alpha$-benzyl glutamate and polyethylene glycol, copolymers of succinate and poly(glycols), polyphosphazene, polyhydroxy-alkanoates and mixtures thereof. Binary and ternary systems are contemplated.

Other specific polymers useful include those marketed under the Medisorb and Biodel trademarks. The Medisorb materials are marketed by the Dupont Company of Wilmington, Del. and are generically identified as a "lactide/glycolide co-polymer" containing "propanoic acid, 2-hydroxy-polymer with hydroxy-polymer with hydroxyacetic acid." Four such polymers include lactide/glycolide 100 L, believed to be 100% lactide having a melting point within the range of 338°-347° F. (170°-175° C.); lactide/glycolide 100 L, believed to be 100% glycolide having a melting point within the range of 437°-455° F. (225°-235° C.); lactide/glycolide 85/15, believed to be 85% lactide and 15% glycolide with a melting point within the range of 338°-347° F. (170°-175° C.); and lactide/glycolide 50/50, believed to be a copolymer of 50% lactide and 50% glycolide with a melting point within the range of 338°-347° F. (170°-175° C.).

Although a variety of different polymers may be used, it may be desired to select polymers to provide a desired viscosity of the mixture prior to drying. For example, if the active or other components are not soluble in the selected solvent, a polymer that will provide a greater viscosity may be desired to assist in maintaining uniformity. On the other hand, if the components are soluble in the solvent, a polymer that provides a lower viscosity may be preferred.

It has also been observed that certain polymers which when used alone would ordinarily require a plasticizer to achieve a flexible film, can be combined without a plasticizer and yet achieve flexible films. For example, HPMC and HPC when used in combination provide a flexible, strong film with the appropriate plasticity and elasticity for manufacturing and storage. No additional plasticizer or polyalcohol is needed for flexibility. Plasticizers may, of course, be used where desirable. The addition of the polymer to the pharmaceutically-active agent imparts excellent stability, even in the form of nanoparticles and/or microparticles.

Controlled Release Films

The term "controlled release" is intended to mean the release of active at a pre-selected or desired rate. This rate will vary depending upon the application. Desirable rates include fast or immediate release profiles as well as delayed, sustained or sequential release. Combinations of release patterns, such as initial spiked release followed by lower levels of sustained release of active are contemplated. Pulsed drug releases are also contemplated.

The polymers that are chosen for the films of the present invention may also be chosen to allow for controlled release, or disintegration, of the active. This may be achieved by providing a substantially water insoluble film that incorporates an active that will be released from the film over time. This may be accomplished by incorporating a variety of different soluble or insoluble polymers and may also include biodegradable polymers in combination. Alternatively, coated controlled release active particles may be incorporated into a readily soluble film matrix to achieve the controlled release property of the active inside the digestive system upon consumption.

Films that provide a controlled release of the active are particularly useful for buccal, gingival, sublingual and vaginal applications. The films of the present invention are particularly useful where mucosal membranes or mucosal fluid is present due to their ability to readily wet and adhere to these areas.

The convenience of administering a single dose of a medication which releases active ingredients in a controlled fashion over an extended period of time as opposed to the administration of a number of single doses at regular intervals has long been recognized in the pharmaceutical arts. The advantage to the patient and clinician in having consistent and uniform blood levels of medication over an extended period of time are likewise recognized. The advantages of a variety of sustained release dosage forms are well known. However, the preparation of a film that provides the controlled release of an active has advantages in addition to those well-known for controlled release tablets. For example, thin films are difficult to inadvertently aspirate and provide an increased patient compliance because they need not be swallowed like a tablet. Moreover, certain embodiments of the inventive films are designed to adhere to the buccal cavity and tongue, where they controllably dissolve. Furthermore, thin films may not be crushed in the manner of controlled release tablets which is a problem leading to abuse of drugs such as Oxycontin.

Other Actives

When an active is introduced to the film, the amount of active per unit area is determined by the uniform distribution of the film. For example, when the films are cut into individual dosage forms, the amount of the active in the dosage form can be known with a great deal of accuracy. This is achieved because the amount of the active in a given area is substantially identical to the amount of active in an area of the same dimensions in another part of the film. The accuracy in dosage is particularly advantageous when the active is a medicament, i.e. a drug.

Preferably the active components of the present invention are those compounds with a melting point below the boiling point of the solvent used. Most preferably, the compounds are lipase inhibitors, such as tetrahydrolipstatin. Any drug having this melting point and that is capable of being formed into the form of nanoparticles and/or microparticles may be included in the present invention. Other active components that may also be incorporated into the films of the present invention include, without limitation, pharmaceutical and cosmetic actives, drugs, medicaments, antigens or allergens such as ragweed pollen, spores, microorganisms, seeds, mouthwash components, and combinations thereof.

A wide variety of medicaments, bioactive active substances and pharmaceutical compositions may be included in the dosage forms of the present invention. Examples of useful drugs include ace-inhibitors, antianginal drugs, anti-arrhythmias, anti-asthmatics, anti-cholesterolemics, analgesics, anesthetics, anti-convulsants, anti-depressants, anti-diabetic agents, anti-diarrhea preparations, antidotes, anti-histamines, anti-hypertensive drugs, anti-inflammatory agents, anti-lipid agents, anti-manics, anti-nauseants, anti-stroke agents, anti-thyroid preparations, anti-tumor drugs, anti-viral agents, acne drugs, alkaloids, amino acid preparations, anti-tussives, anti-uricemic drugs, anti-viral drugs, anabolic preparations, systemic and non-systemic anti-infective agents, anti-neoplastics, anti-parkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumor drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, terine relaxants, anti-obesity drugs, erythropoietic drugs, anti-asthmatics, cough suppressants, mucolytics, DNA and genetic modifying drugs, and combinations thereof.

Examples of medicating active ingredients contemplated for use in the present invention include antacids, $H_2$-antagonists, and analgesics. For example, antacid dosages can be prepared using the ingredients calcium carbonate alone or in combination with magnesium hydroxide, and/or aluminum hydroxide. Moreover, antacids can be used in combination with $H_2$-antagonists.

Analgesics include opiates and opiate derivatives, such as oxycodone (available as Oxycontin®), ibuprofen, aspirin, acetaminophen, and combinations thereof that may optionally include caffeine.

Other preferred drugs for other preferred active ingredients for use in the present invention include anti-diarrheals such as immodium AD, anti-histamines, anti-tussives, decongestants, vitamins, and breath fresheners. Common drugs used alone or in combination for colds, pain, fever, cough, congestion, runny nose and allergies, such as acetaminophen, chlorpheniramine maleate, dextromethorphan, pseudoephedrine HCl and diphenhydramine may be included in the film compositions of the present invention.

Also contemplated for use herein are anxiolytics such as alprazolam (available as Xanax®); anti-psychotics such as clozopin (available as Clozaril®) and haloperidol (available as Haldol®); non-steroidal anti-inflammatories (NSAID's) such as dicyclofenacs (available as Voltaren®) and etodolac (available as Lodine®), anti-histamines such as loratadine (available as Claritin®), astemizole (available as Hismanal™), nabumetone (available as Relafen®), and Clemastine (available as Tavist®); anti-emetics such as granisetron hydrochloride (available as Kytril®) and nabilone (available as Cesamet™); bronchodilators such as Bentolin®, albuterol sulfate (available as Proventil®); anti-depressants such as fluoxetine hydrochloride (available as Prozac®), sertraline hydrochloride (available as Zoloft®), and paroxtine hydrochloride (available as Paxil®); anti-migraines such as Imigra®, ACE-inhibitors such as enalaprilat (available as Vasotec®), captopril (available as Capoten®) and lisinopril (available as Zestril®); anti-Alzheimer's agents, such as nicergoline; and CaH-antagonists such as nifedipine (available as Procardia® and Adalat®), and verapamil hydrochloride (available as Calan®).

Erectile dysfunction therapies include, but are not limited to, drugs for facilitating blood flow to the penis, and for effecting autonomic nervous activities, such as increasing parasympathetic (cholinergic) and decreasing sympathetic (adrenersic) activities. Useful non-limiting drugs include sildenafils, such as Viagra®, tadalafils, such as Cialis®, vardenafils, apomorphines, such as Uprima®, yohimbine hydrochlorides such as Aphrodyne®, and alprostadils such as Caverject®.

The popular H$_2$-antagonists which are contemplated for use in the present invention include cimetidine, ranitidine hydrochloride, famotidine, nizatidien, ebrotidine, mifentidine, roxatidine, pisatidine and aceroxatidine.

Active antacid ingredients include, but are not limited to, the following: aluminum hydroxide, dihydroxyaluminum aminoacetate, aminoacetic acid, aluminum phosphate, dihydroxyaluminum sodium carbonate, bicarbonate, bismuth aluminate, bismuth carbonate, bismuth subcarbonate, bismuth subgallate, bismuth subnitrate, bismuth subsilysilate, calcium carbonate, calcium phosphate, citrate ion (acid or salt), amino acetic acid, hydrate magnesium aluminate sulfate, magaldrate, magnesium aluminosilicate, magnesium carbonate, magnesium glycinate, magnesium hydroxide, magnesium oxide, magnesium trisilicate, milk solids, aluminum mono-ordibasic calcium phosphate, tricalcium phosphate, potassium bicarbonate, sodium tartrate, sodium bicarbonate, magnesium aluminosilicates, tartaric acids and salts.

The pharmaceutically active agents employed in the present invention may include allergens or antigens, such as, but not limited to, plant pollens from grasses, trees, or ragweed; animal danders, which are tiny scales shed from the skin and hair of cats and other furred animals; insects, such as house dust mites, bees, and wasps; and drugs, such as penicillin.

Optional Components

The film of the present invention may additionally include other materials beyond the active agents and polymers. Such other materials may include, without limitation, cosmetic agents, flavors, colors, cooling compounds, encapsulants, anti-foaming agents, anti-oxidants, disintegrants, release agents, sweeteners, surfactants, plasticizers, softeners, additives, and the like.

Cosmetic active agents may include breath freshening compounds like menthol, other flavors or fragrances, especially those used for oral hygiene, as well as actives used in dental and oral cleansing such as quaternary ammonium bases. The effect of flavors may be enhanced using flavor enhancers like tartaric acid, citric acid, vanillin, or the like.

Flavors may be chosen from natural and synthetic flavoring liquids. An illustrative list of such agents includes volatile oils, synthetic flavor oils, flavoring aromatics, oils, liquids, oleoresins or extracts derived from plants, leaves, flowers, fruits, stems and combinations thereof. A non-limiting representative list of examples includes mint oils, cocoa, and citrus oils such as lemon, orange, grape, lime and grapefruit and fruit essences including apple, pear, peach, grape, strawberry, raspberry, cherry, plum, pineapple, apricot or other fruit flavors.

The films containing flavorings may be added to provide a hot or cold flavored drink or soup. These flavorings include, without limitation, tea and soup flavorings such as beef and chicken.

Other useful flavorings include aldehydes and esters such as benzaldehyde (cherry, almond), citral i.e., alphacitral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanol (green fruit), and 2-dodecenal (citrus, mandarin), combinations thereof and the like.

The sweeteners may be chosen from the following non-limiting list: glucose (corn syrup), dextrose, invert sugar, fructose, and combinations thereof; saccharin and its various salts such as the sodium salt; dipeptide sweeteners such as aspartame; dihydrochalcone compounds, glycyrrhizin; brazzein; curculin; erythritol; glycerol; lactitol; miraculin; monellin; pentadin; tagatose; thaumatin; alitame; cyclamate; neotame; *Stevia Rebaudiana* (Stevioside); chloro derivatives of sucrose such as sucralose; sugar alcohols such as sorbitol, mannitol, xylitol, and the like. Also contemplated are hydrogenated starch hydrolysates and the synthetic sweetener 3,6-dihydro-6-methyl-1-1-1,2,3-oxathiazin-4-one-2,2-dioxide, particularly the potassium salt (acesulfame-K), and sodium and calcium salts thereof, and natural intensive sweeteners, such as Lo Han Kuo. Other sweeteners may also be used.

Cooling agents may additionally be incorporated into the films. Such cooling agents may include xylitol, erythritol, dextrose, sorbitol, menthane, menthone, ketals, menthone ketals, menthone glycerol ketals, substituted p-menthanes, acyclic carboxamides, mono menthyl glutarate, substituted cyclohexanamides, substituted cyclohexane carboxamides, substituted ureas and sulfonamides, substituted menthanols, hydroxymethyl and hydroxymethyl derivatives of p-menthane, 2-mercapto-cyclo-decanone, hydroxycarboxylic acids with 2-6 carbon atoms, cyclohexanamides, menthyl acetate, menthyl salicylate, N,2,3-trimethyl-2-isopropyl butanamide (WS-23), N-ethyl-p-menthane-3-carboxamide (WS-3), isopulegol, 3-(1-menthoxy)propane-1,2-diol, 3-(1-menthoxy)-2-methylpropane-1,2-diol, p-menthane-2,3-diol, p-menthane-3,8-diol, 6-isopropyl-9-methyl-1,4-dioxaspiro[4,5]decane-2-methanol, menthyl succinate and its alkaline earth metal salts, trimethylcyclohexanol, N-ethyl-2-isopropyl-5-methyl-cyclohexanecarboxamide, Japanese mint oil, peppermint oil, 3-(1-menthoxy)ethan-1-ol, 3-(1-menthoxy)propan-1-ol, 3-(1-menthoxy)butan-1-ol, 1-menthylacetic acid N-ethylamide, 1-menthyl-4-hydroxypentanoate, 1-menthyl-3-hydroxybutyrate, N,2,3-trimethyl-2-(1-methylethyl)-butanamide, n-ethyl-t-2-c-6 nonadienamide, N,N-dimethyl menthyl succinamide, substituted p-menthanes, substituted p-menthane-carboxamides, 2-isopropanyl-5-methylcyclohexanol (from Hisamitsu Pharmaceuticals, hereinafter "isopregol"); menthone glycerol ketals (FEMA 3807, tradename FRESCOLAT® type MGA); 3-1-menthoxypropane-1,2-diol (from Takasago, FEMA 3784); and menthyl lactate; (from Haarman & Reimer, FEMA 3748, tradename FRESCOLAT® type ML), WS-30, WS-5, WS-14, Eucalyptus extract (p-Mehtha-3,8-Diol), Menthol (its natural or synthetic derivatives), Menthol PG carbonate, Menthol EG carbonate, Menthol glyceryl ether, N-tertbutyl-p-menthane-3-carboxamide, P-menthane-3-carboxylic acid glycerol ester, Methyl-2-isopryl-bicyclo (2.2.1), Heptane-2-carboxamide; and Menthol methyl ether, and menthyl pyrrolidone carboxylate among others.

When the active is combined with the polymer in the solvent, the type of matrix that may be formed depends on the solubilities of the active and the polymer. If the active and/or polymer are soluble in the selected solvent, this may form a solution. However, if the components are not soluble, the matrix may be classified as an emulsion, a colloid, or a suspension.

Also color additives can be used in preparing the films. Such color additives include food, drug and cosmetic colors (FD&C), drug and cosmetic colors (D&C), or external drug and cosmetic colors (Ext. D&C). These colors are dyes, their corresponding lakes, and certain natural and derived colorants. Lakes are dyes absorbed on aluminum hydroxide.

Other examples of coloring agents include known azo dyes, organic or inorganic pigments, or coloring agents of natural origin. Inorganic pigments are preferred, such as the oxides of iron or titanium, these oxides, being added in concentrations ranging from about 0.001 to about 10%, and preferably about 0.5 to about 3%, based on the weight of all the components.

An anti-oxidant may also be added to the film to prevent the degradation of an active, especially where the active is photosensitive.

Anti-foaming and/or, de-foaming components may also be used with the films of the present invention. These components aid in the removal of air, such as entrapped air, from the film-forming compositions. As described above, such entrapped air may lead to non-uniform films. Simethicone is one particularly useful anti-foaming and/or de-foaming agent. The present invention, however, is not so limited and other anti-foam and/or de-foaming agents may suitable be used.

Simethicone may be added to the film-forming mixture as an anti-foaming agent in an amount from about 0.01 weight percent to about 5.0 weight percent, more desirably from about 0.05 weight percent to about 2.5 weight percent, and most desirably from about 0.1 weight percent to about 1.0 weight percent.

A variety of other components and fillers may also be added to the films of the present invention. These may include, without limitation, surfactants; plasticizers which assist in compatibilizing the components within the mixture; polyalcohols; encapsulants; and thermo-setting gels such as pectin, carageenan, and gelatin, which help in maintaining the dispersion of components.

The variety of additives that can be incorporated into the inventive compositions may provide a variety of different functions. Examples of classes of additives include excipients, lubricants, buffering agents, stabilizers, blowing agents, pigments, coloring agents, fillers, bulking agents, sweetening agents, flavoring agents, fragrances, release modifiers, adjuvants, plasticizers, flow accelerators, mold release agents, polyols, granulating agents, diluents, binders, buffers, absorbents, glidants, adhesives, anti-adherents, acidulants, softeners, resins, demulcents, solvents, surfactants, emulsifiers, elastomers and mixtures thereof. These additives may be added with the active ingredient(s).

Useful additives include, for example, gelatin, vegetable proteins such as sunflower protein, soybean proteins, cotton seed proteins, peanut proteins, grape seed proteins, whey proteins, whey protein isolates, blood proteins, egg proteins, acrylated proteins, water-soluble polysaccharides such as alginates, carrageenans, guar gum, agar-agar, xanthan gum, gellan gum, gum arabic and related gums (gum ghatti, gum karaya, gum tragancanth), pectin, water-soluble derivatives of cellulose: alkylcelluloses hydroxyalkylcelluloses and hydroxyalkylalkylcelluloses, such as methylcelulose, hydroxymethylcellulose, hydroxyethylcellulose, hydroxypropylcellulose, hydroxyethylmethylcellulose, hydroxybutylmethylcellulose, cellulose esters and hydroxyalkylcellulose esters such as cellulose acetate phthalate (CAP), hydroxypropylmethylcellulose (HPMC); carboxyalkylcelluloses, carboxyalkylalkylcelluloses, carboxyalkylcellulose esters such as carboxymethylcellulose and their alkali metal salts; water-soluble synthetic polymers such as polyacrylic acids and polyacrylic acid esters, polymethacrylic acids and polymethacrylic acid esters, polyvinylacetates, polyvinylalcohols, polyvinylacetatephthalates (PVAP), polyvinylpyrrolidone (PVP), PVY/vinyl acetate copolymer, and polycrotonic acids; also suitable are phthalated gelatin, gelatin succinate, crosslinked gelatin, shellac, water soluble chemical derivatives of starch, cationically modified acrylates and methacrylates possessing, for example, a tertiary or quaternary amino group, such as the diethylaminoethyl group, which may be quaternized if desired; and other similar polymers.

Such additives may optionally be added in any desired amount desirably within the range of up to about 80%, desirably about 3% to 50% and more desirably within the range of 3% to 20% based on the weight of all components.

Further additives may be inorganic fillers, such as the oxides of magnesium aluminum, silicon, titanium, etc. desirably in a concentration range of about 0.02% to about 3% by weight and desirably about 0.02% to about 1% based on the weight of all components.

Further examples of additives are plasticizers which include polyalkylene oxides, such as polyethylene glycols, polypropylene glycols, polyethylene-propylene glycols, organic plasticizers with low molecular weights, such as glycerol, glycerol monoacetate, diacetate or triacetate, triacetin, polysorbate, cetyl alcohol, propylene glycol, sorbitol, sodium diethylsulfosuccinate, triethyl citrate, tributyl citrate, and the like, added in concentrations ranging from about 0.5% to about 30%, and desirably ranging from about 0.5% to about 20% based on the weight of the polymer.

There may further be added compounds to improve the flow properties of the starch material such as animal or vegetable fats, desirably in their hydrogenated form, especially those which are solid at room temperature. These fats desirably have a melting point of 50° C. or higher. Preferred are tri-glycerides with $C_{12}$-, $C_{14}$-, $C_{16}$-, $C_{18}$-, $C_{20}$- and $C_{22}$-fatty acids. These fats can be added alone without adding extenders or plasticizers and can be advantageously added alone or together with mono- and/or di-glycerides or phosphatides, especially lecithin. The mono- and di-glycerides are desirably derived from the types of fats described above, i.e. with $C_{12}$-, $C_{14}$-, $C_{16}$-, $C_{18}$-, $C_{20}$- and $C_{22}$-fatty acids.

The total amounts used of the fats, mono-, di-glycerides and/or lecithins are up to about 5% and preferably within the range of about 0.5% to about 2% by weight of the total composition It may be further useful to add silicon dioxide, calcium silicate, or titanium dioxide in a concentration of about 0.02% to about 1% by weight of the total composition. These compounds act as texturizing agents.

These additives are to be used in amounts sufficient to achieve their intended purpose. Generally, the combination of certain of these additives will alter the overall release profile of the active ingredient and can be used to modify, i.e. impede or accelerate the release.

Lecithin may be one surface active agent for use in the present invention. Lecithin can be included in the feedstock in an amount of from about 0.25% to about 2.00% by weight. Other surface active agents, i.e. surfactants, include, but are not limited to, cetyl alcohol, sodium lauryl sulfate, the Spans™ and Tweens™ which are commercially available from ICI Americas, Inc. Ethoxylated oils, including ethoxylated castor oils, such as Cremophor® EL which is commercially available from BASF, are also useful. Carbowax™ may be yet another modifier which is very useful in the present invention. Tweens™ or combinations of surface active agents may be used to achieve the desired hydrophilic-lipophilic balance ("HLB"). The present invention, however, does not require the use of a surfactant and films or film-forming compositions of the present invention may be essentially free of a surfactant while still providing the desirable uniformity features of the present invention.

As additional modifiers which enhance the procedure and product of the present invention are identified, Applicants intend to include all such additional modifiers within the scope of the invention claimed herein.

Furthermore, particles or particulates may be added to the film-forming composition or matrix after the composition or matrix may be cast into a film. For example, particles may be added to the film prior to the drying of the film. Particles may be controllably metered to the film and disposed onto the film through a suitable technique, such as through the use of a doctor blade (not shown) which is a device which marginally or softly touches the surface of the film and controllably disposes the particles onto the film surface. Other suitable, but non-limiting, techniques include the use of an additional roller to place the particles on the film surface, spraying the particles onto the film surface, and the like. The particles may be placed on either or both of the opposed film surfaces, i.e., the top and/or bottom film surfaces. Desirably, the particles are securably disposed onto the film, such as being embedded into the film. Moreover, such particles are desirably not fully encased or fully embedded into the film, but remain exposed to the surface of the film, such as in the case where the particles are partially embedded or partially encased.

The particles may be any useful organoleptic agent, cosmetic agent, pharmaceutical agent, or combinations thereof. Desirably, the pharmaceutical agent may be a taste-masked or a controlled-release pharmaceutical agent. Useful organoleptic agents include flavors and sweeteners. Useful cosmetic agents include breath freshening or decongestant agents, such as menthol, including menthol crystals.

Other ingredients include binders which contribute to the ease of formation and general quality of the films. Non-limiting examples of binders include starches, pregelatinize starches, gelatin, polyvinylpyrrolidone, methylcellulose, sodium carboxymethylcellulose, polyacrylamides, polyvinyloxoazolidone, and polyvinylalcohols.

Dosages

The film products of the present invention are capable of accommodating a wide range of amounts of the active ingredient. The films are capable of providing an accurate dosage amount (determined by the size of the film and concentration of the active in the original polymer/water combination) regardless of whether the required dosage may be high or extremely low. Therefore, depending on the type of active or pharmaceutical composition that is incorporated into the film, the active amount may be as high as about 300 mg, desirably up to about 60 mg or as low as the microgram range, or any amount therebetween. Preferably, the film product of the present invention incorporates between 0.1-60% pharmaceutically active agent, and most preferably approximately 60% active agent.

The film products and methods of the present invention are well suited for high potency, low dosage drugs. Drugs in a form described herein, such as in the form of a collection of nanoparticles or microparticles or combinations thereof, allow for a lower dosage amount than would normally be required of the drug in its natural form to achieve a bioequivalent result. This is due to the ease of breaking down a drug in the small-scale form for ingestion into the bodily system, as compared to the difficulty of breaking a larger structure having a lower surface area ratio. The increased surface area of the drug as prepared herein allows for more ready and complete dissolution in the solvent, and thus allows for a more simple ingestion into the bodily system. Further, the apparent solubility of the drug is increased by the process of the invention, as is the equilibrium between the dissolved drug in the solvent. Thus, films of the present invention are well suited for drugs in a traditionally less stable, small-scale form described herein.

The dosages described herein can be used with at least about 10% less dosage amount as compared to the standard dosage amount to achieve the same effect. A standard dosage amount as used herein means the blood level, bioavailability level, or any FDA-approved level of the pharmaceutically active agent. Film compositions using the stabilized nanoparticles and/or microparticles of compounds as described herein have an increased biological effect over that normally seen via conventional methods.

Forming the Film

A number of techniques may be employed in the mixing stage to prevent bubble inclusions in the final film. To provide a composition mixture with substantially no air bubble formation in the final product, anti-foaming or surface-tension reducing agents are employed. Additionally, the speed of the mixture may be desirably controlled to prevent cavitation of the mixture in a manner which pulls air into the mix. Finally, air bubble reduction can further be achieved by allowing the mix to stand for a sufficient time for bubbles to escape prior to drying the film. Desirably, the inventive process first forms a masterbatch of film-forming components without active ingredients such as drug particles or volatile materials such as flavor oils. The actives are added to smaller mixes of the masterbatch just prior to casting. Thus, the masterbatch pre-mix can be allowed to stand for a longer time without concern for instability in drug or other ingredients.

The films of the present invention are preferably formed into a sheet prior to drying. After the desired components are combined to form a multi-component matrix, including the polymer, water, and the pharmaceutically active compound or other components as desired, the combination may be formed into a sheet or film, by any method known in the art such as extrusion, coating, spreading, casting or drawing the multi-component matrix. If a multi-layered film is desired, this may be accomplished by co-extruding more than one combination of components which may be of the same or different composition. A multi-layered film may also be achieved by coating, spreading, or casting a combination onto an already formed film layer.

Although a variety of different film-forming techniques may be used, it may be desirable to select a method that will provide a flexible film, such as reverse roll coating. The flexibility of the film allows for the sheets of film to be rolled and transported for storage or prior to being cut into individual dosage forms. Desirably, the films will also be selfsupporting or in other words able to maintain their integrity and structure in the absence of a separate support. Furthermore, the films of the present invention may be selected of materials that are edible or ingestible.

Coating or casting methods are particularly useful for the purpose of forming the films of the present invention. Specific examples include reverse roll coating, gravure coating, immersion or dip coating, metering rod or meyer bar coating, slot die or extrusion coating, gap or knife over roll coating, air knife coating, curtain coating, or combinations thereof, especially when a multi-layered film is desired.

Roll coating, or more specifically reverse roll coating, is particularly desired when forming films in accordance with the present invention. In this procedure, the coating material may be measured onto the applicator roller by the precision setting of the gap between the upper metering roller and the application roller below it. The coating may be transferred from the application roller to the substrate as it passes around the support roller adjacent to the application roller. Both three roll and four roll processes are common.

The gravure coating process relies on an engraved roller running in a coating bath, which fills the engraved dots or lines of the roller with the coating material. The excess coating on the roller may be wiped off by a doctor blade and the coating may be then deposited onto the substrate as it passes between the engraved roller and a pressure roller. Offset Gravure is common, where the coating is deposited on an intermediate roller before transfer to the substrate.

In the simple process of immersion or dip coating, the substrate may be dipped into a bath of the coating, which is normally of a low viscosity to enable the coating to run back into the bath as the substrate emerges.

In the metering rod coating process, an excess of the coating may be deposited onto the substrate as it passes over the bath roller. The wire-wound metering rod, sometimes known as a Meyer Bar, allows the desired quantity of the coating to remain on the substrate. The quantity is determined by the diameter of the wire used on the rod.

In the slot die process, the coating may be squeezed out by gravity or under pressure through a slot and onto the substrate. If the coating is 100% solids, the process is termed "extrusion" and in this case, the line speed is frequently much faster than the speed of the extrusion. This enables coatings to be considerably thinner than the width of the slot.

The gap or knife over roll process relies on a coating being applied to the substrate which then passes through a "gap" between a "knife" and a support roller. As the coating and substrate pass through, the excess is scraped off.

Air knife coating is where the coating is applied to the substrate and the excess is "blown off" by a powerful jet from the air knife. This procedure is useful for aqueous coatings.

In the curtain coating process, a bath with a slot in the base allows a continuous curtain of the coating to fall into the gap between two conveyors. The object to be coated is passed along the conveyor at a controlled speed and so receives the coating on its upper face.

Drying the Film

A controlled drying process is particularly important when, in the absence of a viscosity increasing composition or a composition in which the viscosity is controlled, for example by the selection of the polymer, the components within the film may have an increased tendency to aggregate or conglomerate. An alternative method of forming a film with an accurate dosage, that would not necessitate the controlled drying process, would be to cast the films on a predetermined well.

When a controlled or rapid drying process is desired, this may be through a variety of methods. A variety of methods may be used including those that require the application of heat. The liquid carriers are removed from the film in a manner such that the uniformity, or more specifically, the non-self-aggregating uniform heterogeneity, that is obtained in the wet film is maintained.

Desirably, the film may be dried from the bottom of the film to the top of the film. Desirably, substantially no air flow is present across the top of the film during its initial setting period, during which a solid, visco-elastic structure is formed. This can take place within the first few minutes, e.g. about the first 0.5 to about 4.0 minutes of the drying process. Controlling the drying in this manner, prevents the destruction and reformation of the film's top surface, which results from conventional drying methods. This may be accomplished by forming the film and placing it on the top side of a surface having top and bottom sides. Then, heat may be initially applied to the bottom side of the film to provide the necessary energy to evaporate or otherwise remove the liquid carrier. The films dried in this manner dry more quickly and evenly as compared to air-dried films, or those dried by conventional drying means. In contrast to an air-dried film that dries first at the top and edges, the films dried by applying heat to the bottom dry simultaneously at the center as well as at the edges. This also prevents settling of ingredients that occurs with films dried by conventional means.

The temperature at which the films are dried may be about 100° C. or less, desirably about 90° C. or less, and most desirably about 80° C. or less.

Another method of controlling the drying process, which may be used alone or in combination with other controlled methods as disclosed above includes controlling and modifying the humidity within the drying apparatus where the film is being dried. In this manner, the premature drying of the top surface of the film is avoided.

Additionally, it has also been discovered that the length of drying time can be properly controlled, i.e. balanced with the heat sensitivity and volatility of the components, and particularly the flavor oils and drugs. The amount of energy, temperature and length and speed of the conveyor can be balanced to accommodate such actives and to minimize loss, degradation or ineffectiveness in the final film. Desirably, the drying of the film will occur within about ten minutes or fewer, or more desirably within about five minutes or fewer.

The films may initially have a thickness of about 500 μm to about 1,500 μm, or about 20 mils to about 60 mils, and when dried have a thickness from about 3 μm to about 250 μm, or about 0.1 mils to about 10 mils. Desirably, the dried films will have a thickness of about 2 mils to about 8 mils, and more desirably, from about 3 mils to about 6 mils.

Uses of Thin Films

The thin films of the present invention are well suited for many uses. The high degree of uniformity of the components of the film makes them particularly well suited for incorporating pharmaceuticals. Furthermore, the polymers used in construction of the films may be chosen to allow for a range of disintegration times for the films. A variation or extension in the time over which a film will disintegrate may achieve control over the rate that the active is released, which may allow for a sustained release delivery system. In addition, the films may be used for the administration of an active to any of several body surfaces, especially those including mucous membranes, such as oral, anal, vaginal, ophthalmological, the surface of a wound, either on a skin surface or within a body such as during surgery, and similar surfaces. Buccal and sublingual administration routes may be particularly useful.

The films may be used to orally administer an active. This may be accomplished by preparing the films as described above and introducing them to the oral cavity of a mammal. This film may be prepared and adhered to a second or support layer from which it may be removed prior to use, i.e. introduction to the oral cavity. An adhesive may be used to attach the film to the support or backing material which may be any of those known in the art, and is preferably not water soluble. If an adhesive is used, it will desirably be a food grade adhesive that is ingestible and does not alter the properties of the active. Mucoadhesive compositions are particularly useful. The film compositions in many cases serve as mucoadhesives themselves.

The films may be applied under or to the tongue of the mammal. When this is desired, a specific film shape, corresponding to the shape of the tongue may be preferred. Therefore the film may be cut to a shape where the side of the film corresponding to the back of the tongue will be longer than the side corresponding to the front of the tongue. Specifically, the desired shape may be that of a triangle or trapezoid. Desirably, the film will adhere to the oral cavity preventing it from being ejected from the oral cavity and permitting more of the active to be introduced to the oral cavity as the film dissolves.

The films of the present invention are desirably packaged in sealed, air and moisture resistant packages to protect the active from exposure oxidation, hydrolysis, volatilization and interaction with the environment. A dispenser may be used, which contains a full supply of the medication typically prescribed for the intended therapy, but due to the thinness of the film and package, is smaller and more convenient than traditional bottles used for tablets, capsules and liquids. Moreover, the films of the present invention dissolve rapidly upon contact with saliva or mucosal membrane areas, eliminating the need to wash the dose down with water. Desirably, a series of such unit doses are packaged together in accordance with the prescribed regimen or treatment, e.g., a 10-90 day supply, depending on the particular therapy. The individual films can be packaged on a backing and peeled off for use.

The embodiment of the present invention including tetrahydrolipstatin refers to a method of treatment and prevention of obesity in individuals. Such method includes providing a film system with a pharmaceutically active dosage of tetrahydrolipstatin to an individual for ingestion of the film system. The active dosage of tetrahydrolipstatin may be present in a small-scale form, such as in the form of nanoparticles or microparticles or combinations thereof, in at least one water soluble polymer.

The features and advantages of the present invention are more fully shown by the following examples which are provided for purposes of illustration, and are not to be construed as limiting the invention in any way.

EXAMPLES

Example 1

Preparation of 60% Tetrahydrolipstatin in 50 mg Film

In a glass bowl was added a mixture of 0.162 g titanium dioxide USP 3328 (Whittaker), 0.002 g Blue #1, and 33.75 g distilled water. The bowl was equipped with a heating mantle and the heat was turned on. The mixture was stirred at 200 rpm for 8 minutes. The temperature was raised to 88° C. A blend of 1.214 g HPMC E50, 1.214 g HPMC E15, 1.458 g polyethylene oxide WSR 1180, 0.972 g erythritol (Cargill), 9.75 g tetrahydrolipstatin (Molcon Corp. Lot 070101) and 0.325 g sucralose was prepared separately. The above blend was added to the heated water mixture and stirred at 200 rpm for 4 minutes. The heating mantle was turned off. The mixture was then stirred at 150 rpm for 20 minutes, and 0.162 g menthol FK-5364 (Ungerer) was added. The temperature was reduced to 38° C. Using the Degussa Dental Multivac Compact, the mixture was stirred at 125 rpm in a 60% vacuum. The vacuum was raised to 90% and the mixture was stirred at 125 rpm for 20 minutes. The vacuum was then raised to 95% and the mixture was stirred at 125 rpm for 8 minutes. The vacuum was then raised to 100% and the mixture was stirred at 125 rpm for 12 minutes. A solution of 0.016 g butylated hydroxytoluene and 0.975 g peppermint 2303 (Ungerer) was added to the mixture. The mixture was stirred at 125 rpm for 4 minutes in a 100% vacuum.

The solution as prepared above was cast into films using the K-Control Coater, with the micrometer adjustable wedge bar set at 320 microns onto the HDP side of 6330. The film was dried for 15 minutes in an 80° C. oven using the drying methods disclosed herein to maintain compositional uniformity. The resulting film was cut into ⅞×1.25 inch strips which weighed approximately 49-52 mg each. The resulting film had an adequate adhesion rating of 3 from HDP side of 6330, moderate tear resistance, adequate strength when pulled, fast dissolution in the mouth, no bitterness, fair flavor, and passed the 180° bend test (the film was bent to 180° without breaking).

Example 2

Preparation of 60% Tetrahydrolipstatin in 100 mg Film

The solution was prepared as in Example 1. The solution was cast into film using the K-Control Coater with the micrometer adjustable wedge bar set at 510 microns onto the HDP side of 6330. The film was dried at 17 minutes in an 80° C. oven using the drying methods disclosed herein to maintain compositional uniformity. The resulting film was cut into ⅞×1.5 inch strips, which each weighed approximately 86-89 mg. The film had an adequate adhesion rating of 3 from HDP side of 6330, moderate tear resistance, good strength when pulled, no bitterness, fair flavor, slow dissolution in the mouth, and passed the 180° bend test out of the moisture analyzers.

Example 3

Preparation of 60% Tetrahydrolipstatin in a 100 mg Film

In a glass bowl was added 0.20 g of titanium dioxide USP 3328 (Whittaker), 0.01 g red #40/blue #1 (99:1), and 30 g distilled water. The bowl was equipped with a heating mantle and the heat was turned on. The solution was stirred for 8 minutes at 150 rpm. The temperature was raised to 83° C. Separately a blend of 3.182 g HPMC E15, 1.91 g polyethylene oxide WSR N80, 1.274 g erythritol (Cargill), 12.0 g tetrahydrolipstatin (Molcon Corp. Lot 070101), and 0.40 g sucralose was prepared. The mixture was stirred at 150 rpm for 4 minutes. The mixture was removed from the heating mantle and stirred at 150 rpm for 20 minutes. The temperature was reduced to 40° C., and 0.20 g menthol FK-5364 (Ungerer) was added. Using the Degussa Dental Multivac Compact, the mixture was stirred for 20 minutes at 125 rpm in a 60% vacuum. The mixture was then stirred for 20 minutes at 125 rpm in a 90% vacuum. The mixture was then stirred for 8 minutes at 125 rpm in a 95% vacuum. The mixture was then stirred for 12 minutes at 125 rpm in a 100% vacuum. A solution of 0.02 g butylated hydroxytoluene, 0.562 g raspberry 188z10 (Abelei), and 0.242 g menthol FK-5364 (Ungerer) was added to the mixture. The mixture was then stirred for 4 minutes at 125 rpm in a 100% vacuum.

The solution as prepared above was case into film using the K-Control Coater with the micrometer adjustable wedge bar set at 460 microns onto the HDP side of 6330. The film was dried for 16 minutes in an 80° C. oven using the drying methods disclosed herein to maintain compositional uniformity. The resulting film was cut into ⅞×1.5 inch strips which each weighed approximately 109-114 mg. The viscosity was slightly too high. The film had a film adhesion rating of 3 from HDP side of 6330, it had low to moderate tear resistance, had good flavor and slow dissolution in the mouth. The resulting film strips and active ingredient were stable.

Example 4

Preparation of 60% Tetrahydrolipstatin in a 100 mg Film 35.58 g of the solution as prepared in Example 3 was left in the bowl. 2.264 g of maltitol syrup (Lycasin 80/55) was added to the solution. Also added was 4.6 g of water. The solution was stirred at 125 rpm for 4 minutes in a 100% vacuum. The resulting solution was cast into film using the K-Control Coater with the micrometer adjustable wedge bar set at 490 microns onto the HDP side of 6330. The film was dried for 17 minutes in an 80° C. oven using the drying methods disclosed herein to maintain compositional uniformity. The film was cut into ⅞×1.5 inch strips, which each weighed approximately 115 mg. The film had a film adhesion rating of 3 from HDP side of 6330, had low to moderate tear resistance, adequate strength when pulled, good flavor, and slow dissolution in the mouth. The resulting film strips and active ingredient were stable.

Example 5

Preparation of 65% Tetrahydrolipstatin in a 92.31 mg Film

In a glass bowl was added 1.432 g maltitol syrup (Lycasin 80/55) containing 1.674 g solids and 0.358 g water, 0.20 g titanium dioxide USP 3328 (Whittaker), 0.01 g red #40/blue #1 (99:1), and 29.642 g distilled water. The bowl was equipped with a heating mantle and the heat was turned on. The solution was stirred for 8 minutes at 150 rpm. The heat was raised to 80° C., and the heat was turned off. Separately a blend of 2.682 g HPMC E15, 1.61 g polyethylene oxide WSR N80, 13 g tetrahydrolipstatin (Molcon Corp. Lot 070101), and 0.40 g sucralose was prepared. The blend was added to the solution, and the resulting solution was stirred for 4 minutes at 150 rpm. The bowl was removed from the heating mantle. The solution was then stirred for 20 minutes at 150 rpm, and then 0.20 g menthol FK-5364 (Ungerer) was added. Using the Degussa Dental Multivac Compact, the solution was stirred for 20 minutes at 125 rpm in a 60% vacuum. The solution was then stirred for 20 minutes at 125 rpm in a 90% vacuum. The solution was then stirred for 8 minutes at 125 rpm in a 95% vacuum. The solution was then stirred for 12 minutes at 125 rpm in a 100% vacuum. A solution of 0.02 g butylated hydroxytoluene, 0.562 g raspberry 188z10 (Aberlei) and 0.242 g menthol FK-5364 (Ungerer) was added to the solution. Added to the solution was 4.60 g of water and 16.67 water. The solution was then stirred for 4 minutes at 125 rpm in a 100% vacuum. The solution contained lumps.

Example 6

Preparation of 65% Tetrahydrolipstatin in 92 mg Film

In a glass bowl was added 0.20 g titanium dioxide USP 3328 (Whittaker), 0.01 g red #40/blue #1 (99:1) and 29.821 g distilled water. The bowl was equipped with a heating mantle and the heat was turned on. The solution was stirred for 4 minutes at 150 rpm. The temperature was raised to 46° C., and the heat was turned off. Separately a blend of 2.682 g HPMC E15, 1.61 g polyethylene oxide WSR N80, 0.536 g erythritol (Cargill), 13.0 g tetrahydrolipstatin (Molcon Corp. Lot 070101), and 0.40 g sucralose was prepared. The blend was added to the solution, and the solution was stirred for 4 minutes at 150 rpm. The solution was removed from the heating mantle and 0.20 g menthol FK-5364 (Ungerer) was added. Using the Degussa Dental Multivac Compact, the solution was stirred for 20 minutes at 125 rpm in a 60% vacuum. The solution was then stirred for 20 minutes at 125 rpm in a 90% vacuum. The solution was then stirred for 8 minutes at 125 rpm in a 95% vacuum. 0.717 g maltitol syrup (Lycasin 80/55) containing 0.538 g solids and 0.178 g water, and 1.18 g water were added to the solution. The solution was then stirred for 8 minutes at 100 rpm in a 100% vacuum. A solution of 0.02 g butylated hydroxytoluene, 0.562 g raspberry 188a10 (Abelei), and 0.242 g menthol FK-5364 (Ungerer) was added. The solution was then stirred at 100 rpm for 4 minutes in a 100% vacuum.

The solution as prepared above was cast into film using the K-Control Coater with the micrometer adjustable wedge bar set at 410 microns onto the HDP side of 6330. The film was then dried 16 minutes in an 80° C. oven using the drying methods disclosed herein to maintain compositional uniformity. The film partially crystallized and gave weaker film strength.

Example 7

Preparation of 54% Tetrahydrolipstatin in a 50 mg Film

In a glass bowl was added 0.36 g titanium dioxide USP 3328 (Whittaker), 0.018 g red #40/blue #1 (99:1), and 58.66 g distilled water. The bowl was equipped with a heating mantle and the heat was turned on. The solution was stirred for 8 minutes at 150 rpm. The heat was raised to 83° C. and the mantle was turned off. Separately a blend of 5.728 g HPMC E15, 3.438 g polyethylene oxide WSR N80, 2.294 erythritol (Cargill), 0.72 g sucralose, and 21.6 g tetrahydrolipstatin (Molcon Corp. Lot 070101) was prepared. The blend was added to the solution, and stirred for 4 minutes at 150 rpm. The solution was removed from the heating mantle. The solution was stirred for 20 minutes at 150 rpm, and 0.36 g menthol FK-5364 (Ungerer) and 6.63 g water were added. Using the Degussa Dental Multivac Compact, the solution was stirred for 20 minutes at 100 rpm in a 60% vacuum. The solution was then stirred for 20 minutes at 100 rpm in a 90% vacuum. The solution was then stirred for 8 minutes in a 95% vacuum. The solution was then stirred for 4 minutes at 100 rpm in a 100% vacuum. A solution of 0.036 g butylated hydroxytoluene, 1.012 g raspberry 188a10 (Abelei), and 0.436 g menthol FK-5364 (Ungerer) was added. The solution was then stirred for 4 minutes at 100 rpm in a 100% vacuum. To the solution was added 5.34 g maltitol syrup (Lycasin 80/55) containing 4 g solids and 1.34 g water, and 2.56 g distilled water. The solution was then stirred for 4 minutes at 100 rpm in a 100% vacuum.

The solution as prepared above was cast into film using the K-Control Coater with the micrometer adjustable wedge bar set at 300 microns onto the HDP side of 6330. The film was dried 15 minutes in an 80° C. oven using the drying methods disclosed herein to maintain compositional uniformity. The film was cut into 7/8×1.25 inch strips, which each weighed approximately 51-52 mg. The film had an adhesion rating of 4 from HDP side of 6330, moderate tear resistance, adequate strength when pulled, good flavor, no bitterness, and fast dissolution in the mouth. The film passed the 180° bend test out of the moisture analyzer. Thirty-six strips were packaged individually in foil, thirty were sent for stability testing and six were kept for retention in the refrigerator. The resulting film strips and active ingredient were stable.

Example 8

Preparation of 54% Tetrahydrolipstatin in a 100 mg Film

The solution as prepared in Example 7 was prepared. The solution was cast into film using the K-Control Coater with the micrometer adjustable wedge bar set at 480 microns onto the HDP side of 6330. The film was dried for 17 minutes in an 80° C. oven using the drying methods disclosed herein to maintain compositional uniformity. The film was cut into 7/8×1.5 inch strips, which each weighed approximately 106-108 mg. The film had a film adhesion rating of 4 from HDP side of 6330, moderate tear resistance, good strength when pulled, good flavor, no bitterness, moderate to slow dissolution in the mouth, and passed the 180° bend test out of the moisture analyzer. Thirty-nine strips were packaged individually in foil, and thirty were sent for testing and nine were kept for retention in the refrigerator. The resulting film strips and active ingredient were stable.

Example 9

Preparation of 54% Tetrahydrolipstatin Placebo for Stability Studies

In a glass bowl was added 0.368 g titanium dioxide USP 3328 (Whittaker), 0.018 g red #40/blue #1 (99:1), and 59.838 g distilled water. The bowl was equipped with a heating mantle and the heat was turned on. The solution was stirred for 8 minutes at 150 rpm. The heat was raised to 86° C. and the mantle was turned off. Separately a blend of 5.852 g HPMC E15, 3.513 g polyethylene oxide WSR N80, 2.343 erythritol (Cargill), and 0.736 g sucralose was prepared. The blend was added to the solution, and stirred for 8 minutes at 150 rpm. The solution was removed from the heating mantle and 0.368 g menthol FK-5364 (Ungerer) and 6.82 g water were added. Using the Degussa Dental Multivac Compact, the solution was stirred for 20 minutes at 125 rpm in a 60% vacuum. The solution was then stirred for 20 minutes at 100 rpm in a 90% vacuum. The solution was then stirred for 8 minutes at 100 rpm in a 95% vacuum. The solution was then stirred for 8 minutes at 100 rpm in a 100% vacuum. A solution of 0.037 g butylated hydroxytoluene, 1.034 g raspberry 188a10 (Abelei), and 0.445 g menthol FK-5364 (Ungerer) were added to the solution. To the solution was added 5.449 g maltitol syrup (Lycasin 80/55) containing 4.087 g maltitol and 1.362 g water. 1.07 g distilled water was added to the solution. The solution was then stirred for 4 minutes at 100 rpm in a 100% vacuum.

The solution as prepared above was cast into film using the K-Control Coater with the micrometer adjustable wedge bar set at 440 microns onto the HDP side of 6330. The film was dried for 18 minutes in an 80° C. oven using the drying methods disclosed herein to maintain compositional uniformity. The film was then cut into 7/8×1.5 inch strips, which each weighed approximately 52 mg. Thirty strips were packaged individually in foil and were sent for stability studies. The resulting film strips and active ingredient were stable.

Example 10

Preparation of 54% Tetrahydrolipstatin Formulation by Adding Drug Later

In a glass bowl were added 2.67 g maltitol syrup (Lycasin 80/55) containing 2.00 g solids and 0.67 g water, 0.18 g titanium dioxide USP 3328 (Whittaker), 0.009 g red #40/blue #1 (99:1), and 27.5 g distilled water. The bowl was equipped with a heating mantle and the heat was turned on. The solution was stirred for 8 minutes at 150 rpm. The temperature was raised to 84° C., and the heat was turned off. Separately a blend of 2.864 g HPMC E15, 1.719 g polyethylene oxide WSR N80, 1.147 g erythritol (Cargill), and 0.36 g sucralose was prepared. The blend was added to the solution. The solution was then stirred for 4 minutes at 150 rpm and removed from the heat. The solution was then stirred for 20 minutes at 150 rpm, and 0.18 g menthol FK-5364 (Ungerer) and 3.08 g distilled water were added. Using the Degussa Dental Multivac Compact, the solution was stirred for 20 minutes at 125 rpm in a 60% vacuum. The solution was then stirred for 20 minutes at 100 rpm in a 90% vacuum. The solution was then stirred for 8 minutes at 100 rpm in a 95% vacuum. To the solution was added 0.39 g distilled water. The solution was then stirred for 4 minutes at 100 rpm in a 98% vacuum. The solution was then stirred for 4 minutes at 100 rpm in a 100% vacuum. A solution of 10.8 g tetrahydrolipstatin (Molcon Corp. Lot 070101), 0.018 g butylated hydroxytoluene, 0.506 g raspberry 188a10 (Abelei), 0.218 g menthol FK-5364 (Ungerer), and 1.8 g ethanol was added. The solution temperature was approximately 29° C., which was below the melting point of the tetrahydrolipstatin. The solution was then stirred for 8 minutes at 100 rpm in a 100% vacuum. The solution turned semi solid, showing crystallization of the drug. The bowl was returned to the heating mantle and the heat was turned on. The solution was stirred for 10 minutes, partially stirring at 100 rpm in a 100% vacuum. The temperature was 30° C. The solution was still lumpy, due to crystallization of the drug, and appeared to be overheated in the bottom of the bowl.

Example 11

Preparation of 54% Tetrahydrolipstatin Formulation by Adding Drug Later

In a glass bowl were added 5.728 g maltitol syrup (Lycasin 80/55) containing 4.00 g solids and 1.34 g water, 0.36 g titanium dioxide USP 3328 (Whittaker), 0.018 g red #40/blue #1 (99:1), and 58.66 g distilled water. The bowl was equipped with a heating mantle and the heat was turned on. The solution was stirred for 12 minutes at 150 rpm. The temperature was raised to 85° C., and the bowl was removed from the heat.

Separately a blend of 5.728 g HPMC E15, 3.438 g polyethylene oxide WSR N80, 2.294 g erythritol (Cargill), and 0.72 g sucralose was prepared. The blend was added to the solution. The solution was then stirred for 16 minutes at 150 rpm. The solution was heated to 40° C., and 0.18 g menthol FK-5364 (Ungerer) and 4.93 g distilled water were added. Using the Degussa Dental Multivac Compact, the solution was stirred for 20 minutes at 100 rpm in a 60% vacuum. The solution was then stirred for 20 minutes at 100 rpm in a 90% vacuum. The solution was then stirred for 8 minutes at 100 rpm in a 95% vacuum. The solution was then stirred for 4 minutes at 100 rpm in a 100% vacuum. The bowl was equipped with a heating mantle and the heat was turned on. The solution was then stirred for 8 minutes at 100 rpm in a 100% vacuum, at a temperature of 28° C. The solution was then stirred for 8 minutes at 100 rpm in a 100% vacuum, at a temperature of 30° C. The solution was then stirred for 8 minutes at 100 rpm in a 100% vacuum, at a temperature of 47° C. To the solution was added 21.6 g tetrahydrolipstatin (Molcon Corp. Lot 070101). The solution was then stirred for 4 minutes at 100 rpm in a 90% vacuum, at a temperature of 52° C., which was above the melting point of the tetrahydrolipstatin. The solution was then stirred for 8 minutes at 100 rpm in a 95% vacuum, at a temperature of 47° C. To the solution was added 24.92 g distilled water. The solution was then stirred for 4 minutes at 100 rpm in a 95% vacuum. The solution was then stirred for 4 minutes at 100 rpm in a 100% vacuum at a temperature of 32° C.

The solution was cast into film using the K-Control Coater with the micrometer adjustable wedge bar set at 500 microns onto HDP side of 6330. The film was dried 17 minutes in an 80° C. oven using the drying methods disclosed herein to maintain compositional uniformity. The film was then cut into ⅞×1.5 inch strips, which each weighed approximately 116-123 mg. The film had a film adhesion rating of 4 from the HDP side of 6330, had low to moderate tear resistance, had adequate strength when pulled, slow to moderate dissolution in the mouth, good flavor, no bitterness, and passed the 180° bend test out of the moisture analyzer. The strips were then sealed individually in foil for storage.

What is claimed is:

1. A method of forming a stabilized solid form of a pharmaceutically active agent in a solid matrix wherein said solid form is present in the form of nanoparticles, microparticles, or combinations thereof, with said method comprising the steps of:
   a. providing a mixture of a pharmaceutically active agent having a melting point less than or equal to about 100° C. and at least one water soluble polymer;
   b. adding at least a portion of said mixture to a solvent, said solvent being heated to a temperature above said melting point of said pharmaceutically active agent whereby said active agent melts and forms a liquid dispersion of the active agent in the mixture; and
   c. rapidly evaporating the solvent to form a solid matrix containing a stabilized solid dispersion of said pharmaceutically active agent in said solid matrix, wherein said pharmaceutically active agent is present in the form of nanoparticles, microparticles, or combinations thereof.

2. The method of claim 1, wherein said pharmaceutically active agent is water-insoluble.

3. The method of claim 1, wherein said stabilized, solid form of said pharmaceutically active agent is in a form of a collection or agglomeration of nanoparticles.

4. The method of claim 1, wherein said stabilized, solid form of said pharmaceutically active agent is in a form of a collection of microparticles.

5. The method of claim 1, wherein said pharmaceutically active agent is a lipase inhibitor.

6. The method of claim 1, wherein said polymer is selected from the group consisting of a surfactant polymer, a cellulose polymer, and combinations thereof.

7. The method of claim 1, wherein said solvent is heated to a temperature at least higher than the melting point of the pharmaceutically active agent.

8. The method of claim 1, wherein said pharmaceutically active agent comprises about 0.001 to 60% by weight of the mixture.

9. The method of claim 1, further comprising the step of preparing a pharmaceutical-based film with said stabilized solid form of said pharmaceutically active agent.

10. The method of claim 9, wherein said pharmaceutically active agent is a lipase inhibitor.

11. A method of forming a stabilized solid form of a pharmaceutically active agent in a solid matrix wherein said solid form is present in the form of nanoparticles, microparticles, or combinations thereof, with said method comprising the steps of:
   a. providing a mixture of a pharmaceutically active agent having a melting point less than or equal to about 100° C. and at least one water soluble polymer;
   b. adding at least a portion of said mixture to a solvent, said solvent being heated to a temperature above said melting point of said pharmaceutically active agent whereby said active agent melts and forms a liquid dispersion of the active agent in the mixture; and
   c. rapidly evaporating the solvent to form a solid matrix containing a stabilized solid dispersion of said pharmaceutically active agent in said solid matrix, wherein said pharmaceutically active agent is present in the form of nanoparticles, microparticles, or combinations thereof; and
   d. gathering the resulting residue, wherein said resulting residue comprises said pharmaceutically active agent in the form of nanoparticles, microparticles, or combinations thereof.

12. The method of claim 11, wherein said pharmaceutically active agent is a lipase inhibitor.

13. The method of claim 11, wherein said pharmaceutically active agent is water-insoluble.

14. The method of claim 11, wherein said polymer is selected from the group consisting of a surfactant polymer, a cellulose polymer and combinations thereof.

15. The method of claim 11, wherein said solvent is heated to a temperature at least higher than the melting point of the pharmaceutically active agent.

16. The method of claim 11, wherein said pharmaceutically active agent comprises about 0.001 to 60% by weight of the mixture.

17. The method of claim 11, wherein said residue comprises said pharmaceutically active agent in the form of a collection or agglomeration of nanoparticles.

18. The method of claim 11, wherein said residue comprises said pharmaceutically active agent in the form of microparticles.

19. The method of claim 11, further comprising the step of preparing a pharmaceutical-based film with said residue.

20. The method of claim 19, wherein said pharmaceutically active agent is a lipase inhibitor.

21. A method for preparing a pharmaceutically-based film which comprises forming a film containing a stabilized solid form as produced in claim 11.

22. The method of claim 21, wherein said pharmaceutically active agent is a lipase inhibitor.

23. The method of claim 21, wherein said pharmaceutically active agent is water-insoluble.

24. The method of claim 21, wherein said polymer is selected from the group consisting of a surfactant polymer, a cellulose polymer, and combinations thereof.

25. The method of claim 21, wherein said pharmaceutically active agent is in a form of a collection of nanoparticles.

26. The method of claim 21, wherein said pharmaceutically active agent is in a form of a collection of microparticles.

27. The method of claim 21, wherein said solvent is heated to a temperature at least higher than the melting point of the pharmaceutically active agent.

28. The method of claim 21, wherein said pharmaceutically active agent comprises about 0.001% to about 60% by weight of the mixture.

29. The method of claim 21, wherein said stabilized solid form is in the form of nanoparticles.

30. The method of claim 29, wherein said nanoparticles agglomerate together to form microparticles of pharmaceutically active agent.

31. The method of claim 30, wherein said agglomerated microparticles are about 2 to about 4 microns in size.

32. The method of claim 29, wherein said pharmaceutically active agent is a lipase inhibitor.

33. The method of claim 29, wherein said polymer is selected from the group consisting of a surfactant polymer, a cellulose polymer, and combinations thereof.

34. The method of claim 29, wherein said solvent is heated to a temperature at least higher than the melting point of the pharmaceutically active agent.

35. The method of claim 29, wherein said pharmaceutically active agent comprises about 0.001 to 60% by weight of the mixture.

36. The method of claim 21, wherein said stabilized solid form is in the form of microparticles.

37. The method of claim 36, wherein said microparticles are about 2 to about 4 microns in size.

38. The method of claim 36, wherein said pharmaceutically active agent is a lipase inhibitor.

39. The method of claim 36, wherein said polymer is selected from the group consisting of a surfactant polymer, a cellulose polymer, and combinations thereof.

40. The method of claim 36, wherein said solvent is heated to a temperature at least higher than the melting point of the pharmaceutically active agent.

41. The method of claim 36, wherein said pharmaceutically active agent comprises about 0.001 to 60% by weight of the mixture.

42. The method of claim 1, wherein said solvent is selected from the group consisting of water, organic solvents, and combinations thereof.

43. The method of claim 11, wherein said solvent is selected from the group consisting of water, organic solvents, and combinations thereof.

44. The method of claim 21, wherein said solvent is selected from the group consisting of water, organic solvents, and combinations thereof.

45. The method of claim 29, wherein said solvent is selected from the group consisting of water, organic solvents, and combinations thereof.

46. The method of claim 36 wherein said solvent is selected from the group consisting of water, organic solvents, and combinations thereof.

\* \* \* \* \*